United States Patent [19]

Lee et al.

[11] Patent Number: 5,639,742

[45] Date of Patent: Jun. 17, 1997

[54] 9-[(SUBSTITUTED GLYCYL)AMIDO]-6-(SUBSTITUTED)-5-HYDROXY-6-DEOXYTETRACYCLINES

[76] Inventors: Ving Jick Lee, 19 Shuart Rd., Monsey, N.Y. 10952; Brian Lee Buckwalter, 102 Ovington Rd., Yardley, Pa. 19067; Timothy Claude Barden, 3424 Stafford Pl., Holland, Pa. 18966

[21] Appl. No.: 297,464

[22] Filed: Aug. 29, 1994

Related U.S. Application Data

[62] Division of Ser. No. 42,302, Apr. 2, 1993, Pat. No. 5,371,076.

[51] Int. Cl.$^6$ .................... C07C 725/66; A01K 31/65
[52] U.S. Cl. .................... 514/152; 552/201; 552/205
[58] Field of Search .................... 552/204, 205; 514/152

[56] References Cited

U.S. PATENT DOCUMENTS

| | | | |
|---|---|---|---|
| Re. 26,253 | 8/1967 | Petisi | 260/559 |
| Re. 26,271 | 9/1967 | Boothe | 260/559 |
| 2,482,055 | 9/1949 | Duggar | 514/152 |
| 3,007,965 | 11/1961 | Growich | 514/152 |
| 3,043,875 | 7/1962 | Beereboom | 514/152 |
| 3,200,149 | 8/1965 | Blackwood | 514/152 |
| 3,219,671 | 11/1965 | Hlavka et al. | 514/152 |
| 3,226,436 | 12/1965 | Petisi | 514/152 |
| 3,277,172 | 10/1966 | Alicino | 552/205 |
| 3,338,963 | 8/1967 | Petisi | 514/152 |
| 3,341,585 | 9/1967 | Bitha | 514/152 |
| 3,341,586 | 9/1967 | Bitha et al. | 514/152 |
| 3,360,557 | 12/1967 | Shu | 514/152 |
| 3,360,561 | 12/1967 | Zambrano | 514/152 |
| 3,397,230 | 8/1968 | Winterbottom | 552/205 |
| 3,483,251 | 12/1969 | Zambrano | 552/205 |
| 3,518,306 | 6/1970 | Martell | 514/152 |
| 3,579,579 | 5/1971 | Hlavka et al. | 514/152 |
| 3,795,707 | 3/1974 | Luaano | 552/205 |
| 3,829,453 | 8/1974 | Conover et al. | 514/152 |
| 3,849,493 | 11/1974 | Conover | 552/205 |
| 3,993,694 | 11/1976 | Martin | 552/205 |
| 5,021,407 | 6/1991 | Levy | 514/152 |
| 5,281,628 | 1/1994 | Hlavka et al. | 514/152 |
| 5,380,888 | 1/1995 | Sum | 552/205 |

FOREIGN PATENT DOCUMENTS

| | | |
|---|---|---|
| 582788 | 2/1994 | European Pat. Off. . |
| 1100495 | 1/1966 | United Kingdom . |

OTHER PUBLICATIONS

"The Merck Index", 11th Edition, 1989, Merck & Co. Rahway, NJ, USA, p. 541, No. 3429.
WO-A-93 08806 (Trustees of Tufts College) *the whole document*.
EP Search Report for Application No. 94104690.6.
U.S. application No. 07/926,091 Hlauka et al., filed Aug. 1992.
Chopra, handbook of Experimental Pharmacology, vol. 78, 317–392, Springer–Verlag (1985).
Levy, Antimicrobial Agents and Chemotherapy, vol. 33, No. 8, 1373–1374, (Aug. 1989).
Salyers, Molecular Microbiology, 4(1), 151–156 (1990).

*Primary Examiner*—Robert Gerstl

[57] ABSTRACT

The invention provides compounds of the formula:

wherein R, $R^1$, $R^2$ and W are defined in the specification. These compounds are useful as antibiotic agents.

72 Claims, No Drawings

9-[(SUBSTITUTED GLYCYL)AMIDO]-6-(SUBSTITUTED)-5-HYDROXY-6-DEOXYTETRACYCLINES

This is a divisional of application Ser. No. 08/042,302, filed on Apr. 2, 1993, now U.S. Pat. No. 5,371,076.

BACKGROUND OF THE INVENTION

1. Field of the Invention

The invention relates to novel [4S-(4α,4aα,5 α,5aα,6α, 12aα)]-4-(dimethylamino)-6-(substituted)-9-[[(substituted amino)substituted]amino]-1,4,4a,5,5a,6,11,12a-octahydro-3,5,10,12,12a-pentahydroxy-1,11-dioxo-2-naphthacenecarboxamides herein after called 9-[(substituted glycyl)amido]-6-(substituted)-5-hydroxy-6-deoxytetracyclines, which exhibit antibiotic activity against a wide spectrum of organisms including organisms which are resistant to tetracyclines and are useful as antibiotic agents.

The invention also relates to novel 9-[(haloacyl)amido]-6-(substituted)-5-hydroxy-6-deoxytetracycline and novel 9-[(protected aminoacyl)amido]-6-(substituted)-5-hydroxy-6-deoxytetracycline intermediates useful for making the novel compounds of the present invention and to novel methods for producing the novel compounds and intermediate compounds.

SUMMARY OF THE INVENTION

This invention is concerned with novel 9-[(substituted glycyl)amido]-6-(substituted)-5-hydroxy-6-deoxytetracyclines, represented by formula I, which have antibacterial activity; with methods of treating infectious diseases in warm blooded animals employing these new compounds; with pharmaceutical preparations containing these compounds; with novel intermediate compounds and processes for the production of these compounds. More particularly, this invention is concerned with compounds of formula I which have antibacterial activity against tetracycline resistant strains as well as a high level of activity against strains which are normally susceptible to tetracyclines.

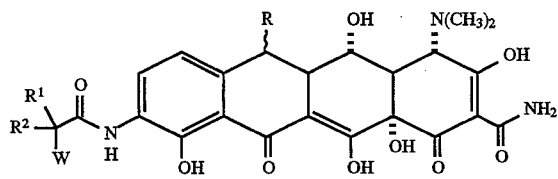

In formula I,

R is selected from methylene, α-$CH_3$ and β-$CH_3$;

$R^1$ is selected from hydrogen; straight or branched ($C_1$–$C_8$) alkyl group selected from methyl, ethyl, propyl, isopropyl, butyl, isobutyl, pentyl, hexyl, heptyl and octyl; straight or branched ($C_1$–$C_8$)alkyl group optionally substituted with α-mercapto, α-(methylthio), α-hydroxy, carboxyl, carboxamido, amino, guanidino or amidino; ($C_6$–$C_{10}$)aryl group selected from phenyl, α-naphthyl and β-naphthyl; substituted ($C_6$–$C_{10}$)aryl group substitution selected from hydroxy, halogen, ($C_1$–$C_4$)alkoxy, trihalo ($C_1$–$C_3$) alkyl, nitro, amino, cyano, ($C_1$–$C_4$) alkoxycarbonyl, ($C_1$–$C_3$)alkylamino and carboxy; ($C_7$–$C_9$)aralkyl group selected from benzyl, 1-phenylethyl, 2-phenylethyl and phenylpropyl; substituted($C_7$–$C_9$)aralkyl group substitution selected from halo, ($C_1$–$C_4$)alkyl, nitro, hydroxy, amino, mono- or di-substituted ($C_1$–$C_4$)alkylamino, ($C_1$–$C_4$)alkoxy, ($C_1$–$C_4$)alkylsulfonyl, cyano and carboxy; (heterocycle) methyl group said heterocycle selected from 4-(or 3-)imidazolyl, 4-(3-)oxazolyl, 3-(or 2-)indolyl, 2-(or 3-) furanyl, 2-(or 3-)thienyl, 2-(or 3-)pyrrolyl, 2-(or 3-)pyrazolyl, 4-(1,2,3-triazolyl) and benzimidazolyl; ($C_3$–$C_6$)cycloalkylmethyl group selected from (cyclopropyl)methyl, (cyclobutyl)methyl, (cyclopentyl) methyl and (cyclohexyl)methyl;

$R^2$ is selected from hydrogen and ($C_1$–$C_6$)alkyl selected from methyl, ethyl, propyl, isopropyl, butyl, isobutyl, pentyl and hexyl;

W is selected from amino; hydroxylamino; ($C_1$–$C_{12}$) straight or branched alkyl monosubstituted amino group substitution selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl, 1-methyl-1-ethylpropyl, heptyl, octyl, nonyl, decyl, undecyl and dodecyl and the diastereomers and enantiomers of said branched alkyl monosubstituted amino group; ($C_3$–$C_8$)cycloalkyl monosubstituted amino group substitution selected from cyclopropyl, trans-1,2-dimethylcyclopropyl, cis-1,2-dimethylcyclopropyl, cyclobutyl, cyclopentyl, cyclohexyl, cycloheptyl, cyclooctyl, bicyclo[2.2.1]hept-2-yl, and bicyclo[2.2.2] oct-2-yl and the diastereomers and enantiomers of said ($C_3$–$C_8$)cycloalkyl monosubstituted amino group; [($C_4$–$C_{10}$)cycloalkyl]($C_1$–$C_3$)alkyl monosubstituted amino group substitution selected from (cyclopropyl) methyl, (cyclopropyl)ethyl, (cyclobutyl)methyl, (trans-2-methylcyclopropyl)methyl, and (cis-2-methylcyclobutyl) methyl; ($C_3$–$C_{10}$)alkenyl monosubstituted amino group substitution selected from allyl, 3-butenyl, 2-butenyl (cis or trans), 2-pentenyl, 4-octenyl, 2,3-dimethyl-2-butenyl, 3-methyl-2-butenyl, 2-cyclopentenyl and 2-cyclohexenyl; ($C_6$–$C_{10}$)aryl monosubstituted amino group substitution selected from phenyl and naphthyl; ($C_7$–$C_{10}$) aralkylamino group selected from benzyl, 2-phenylethyl, 1-phenylethyl, 2-(naphthyl)methyl, 1-(naphthyl)methyl and phenylpropyl; substituted phenyl amino group substitution selected from ($C_1$–$C_5$)acyl, ($C_1$–$C_5$)acylamino, ($C_1$–$C_4$)alkyl, mono or disubstituted ($C_1$–$C_8$)alkylamino, ($C_1$–$C_4$)alkoxy, ($C_1$–$C_4$)alkoxycarbonyl, ($C_1$–$C_4$) alkylsulfonyl, amino, carboxy, cyano, halogen, hydroxy, nitro and trihalo($C_1$–$C_3$)alkyl; straight or branched symmetrical disubstituted ($C_2$–$C_8$)alkylamino group substitution selected from dimethyl, diethyl, diisopropyl, di-n-propyl, di-n-butyl and diisobutyl; symmetrical disubstituted ($C_3$–$C_{14}$)cycloalkylamino group substitution selected from dicyclopropyl, dicyclobutyl, dicyclopentyl, dicylohexyl and dicycloheptyl; straight or branched unsymmetrical disubstituted ($C_3$–$C_{14}$) alkylamino group wherein the total number of carbons in the substitution is not more than 14; unsymmetrical disubstituted ($C_4$–$C_{14}$)cycloalkylamino group wherein the total number of carbons in the substitution is not more than 14; ($C_2$–$C_8$)azacycloalkyl and substituted ($C_2$–$C_8$) azacycloalkyl group selected from aziridinyl, azetidinyl, pyrrolidinyl, piperidinyl, 4-methylpiperidinyl, 2-methylpyrrolidinyl, cis-3,4-dimethylpyrrolidinyl, trans-3,4-dimethylpyrrolidinyl, 2-azabicyclo[2.1.1]hex-2-yl, 5-azabicyclo[2.1.1]hex-5-yl, 2-azabicyclo[2.2.1]hept-2-yl, 7-azabicyclo[2.2.1]hept-7-yl, and 2-azabicyclo[2.2.2] oct-2-yl and the diastereomers and enantiomers of said ($C_2$–$C_8$)azacycloalkyl and substituted ($C_2$–$C_8$)

azacycloalkyl group; 1-azaoxacycloalkyl group selected from morpholinyl and 1-aza-5-oxocycloheptane; substituted 1-azaoxacycloalkyl group substitution selected from 2-($C_1$–$C_3$)alkylmorpholinyl, 2-($C_3$–$C_6$) cycloalkylmorpholinyl, 3-($C_1$–$C_3$)alkylisooxazolidinyl, tetrahydrooxazinyl and 3,4-dihydrooxazinyl; [1,n]-diazacycloalkyl and substituted [1,n]-diazacycloalkyl group selected from piperazinyl, 2-($C_1$–$C_3$) alkylpiperazinyl, 2-($C_3$–$C_6$)cycloalkylpiperazinyl, 4-($C_1$–$C_3$)alkylpiperazinyl, 2,4-dimethylpiperazinyl, 4-($C_1$–$C_4$)alkoxypiperazinyl, 4-($C_6$–$C_{10}$) aryloxypiperazinyl, 4-hydroxypiperazinyl, 2,5-diazabicyclo[2.2.1]hept-2-yl, 2,5-diaza-5-methylbicyclo [2.2.1]hept-2-yl, 2,3-diaza-3-methylbicyclo[2.2.2]oct-2-yl, and 2,5-diaza-5,7-dimethylbicyclo[2.2.2]oct-2-yl and the diastereomers or enantiomers of said [1,n]-diazacycloalkyl and substituted [1,n]-diazacycloalkyl group; 1-azathiacycloalkyl and substituted 1-azathiacycloalkyl group selected from thiomorpholinyl, 2-($C_1$–$C_3$)alkylthiomorpholinyl and 3-($C_3$–$C_6$) cycloalkylthiomorpholinyl; N-azolyl and substituted N-azolyl group selected from 1-imidazolyl, 2-($C_1$–$C_3$) alkyl-1-imidazolyl, 3-($C_1$–$C_3$)alkyl-1-imidazolyl, 1-pyrrolyl, 2-($C_1$–$C_3$)alkyl-1-pyrrolyl, 3-($C_1$–$C_3$)alkyl-1-pyrrolyl, 1-pyrazolyl, 3-($C_1$–$C_3$)-alkyl-1-pyrazolyl, indolyl, 1-(1,2,3-triazolyl), 4-($C_1$–$C_3$)alkyl-1-(1,2,3-triazolyl), 5-($C_1$–$C_3$)alkyl-1-(1,2,3-triazolyl), 4-(1,2,4-triazolyl), 1-tetrazolyl, 2-tetrazolyl and benzimidazolyl; (heterocycle) amino group said heterocycle selected from 2- or 3-furanyl, 2- or 3-thienyl, 2-, 3- or 4-pyridyl, 2- or 5-pyridazinyl, 2-pyrazinyl, 2-(imidazolyl), (benzimidazolyl), and (benzothiazolyl) and substituted (heterocycle)amino group (substitution selected from straight or branched ($C_1$–$C_6$)alkyl); (heterocycle) methylamino group selected from 2- or 3-furylmethylamino, 2- or 3-thienylmethylamino, 2-, 3- or 4-pyridylmethylamino, 2- or 5-pyridazinylmethylamino, 2-pyrazinylmethylamino, 2-(imidazolyl)methylamino, (benzimidazolyl) methylamino, and (benzothiazolyl)methylamino and substituted (heterocycle)methylamino group (substitution selected from straight or branched ($C_1$–$C_6$)alkyl); carboxy ($C_2$–$C_4$)alkylamino group selected from aminoacetic acid, α-aminopropionic acid, β-aminopropionic acid, α-butyric acid, and β-aminobutyric acid and the enantiomers of said carboxy ($C_2$–$C_4$)alkylamino group; ($C_1$–$C_4$) alkoxycarbonylamino group selected from methoxycarbonylamino, ethoxycarbonylamino, allyloxycarbonylamino, propoxycarbonylamino, isoproproxycarbonylamino, 1,1-dimethylethoxycarbonylamino, n-butoxycarbonylamino, and 2-methylpropoxycarbonylamino; ($C_1$–$C_4$)alkoxyamino group selected from methoxyamino, ethoxyamino, n-propoxyamino, 1-methylethoxyamino, n-butoxyamino, 2-methylpropoxyamino, and 1,1-dimethylethoxyamino; ($C_3$–$C_8$)cycloalkoxyamino group selected from cyclopropoxy, trans-1, 2-dimethylcyclopropoxy, cis-1,2-dimethylcyclopropoxy, cyclobutoxy, cyclopentoxy, cyclohexoxy, cycloheptoxy, cyclooctoxy, bicyclo[2.2.1] hept-2-yloxy, and bicyclo[2.2.2]oct-2-yloxy and the diastereomers and enantiomers of said ($C_3$–$C_8$) cycloalkoxyamino group; ($C_6$–$C_{10}$)aryloxyamino group selected from phenoxyamino, 1-naphthyloxyamino and 2-naphthyloxyamino; ($C_7$–$C_{11}$)arylalkoxyamino group substitution selected from benzyloxy, 2-phenylethoxy, 1-phenylethoxy, 2-(naphthyl)methoxy, 1-(naphthyl) methoxy, and phenylpropoxy; or $R^1$ and W taken together are —$CH_2(CH_2)_nCH_2NH$—, wherein n=1–3; and the pharmacologically acceptable organic and inorganic salts or metal complexes. It will be appreciated that when $R^1$ does not equal $R^2$ the stereochemistry of the asymmetric carbon (i.e. the carbon bearing the W substituent) maybe be either the racemate (DL) or the individual enantiomers (L or D).

Preferred compounds are compounds according to the above formula I, wherein:

R is selected from methylene, α-$CH_3$ and β-$CH_3$;

$R^1$ is selected from hydrogen; straight or branched ($C_1$–$C_8$) alkyl group selected from methyl, ethyl, propyl, isopropyl, butyl, isobutyl, pentyl, hexyl, heptyl and octyl; straight or branched ($C_1$–$C_8$)alkyl group optionally substituted with α-mercapto, α-(methylthio), α-hydroxy, carboxyl, carboxamido, amino, guanidino or amidino; ($C_6$–$C_{10}$)aryl group selected from phenyl, α-naphthyl and β-naphthyl; ($C_7$–$C_9$)aralkyl group selected from benzyl, 1-phenylethyl, 2-phenylethyl and phenylpropyl; substituted($C_7$–$C_9$)aralkyl group substitution selected from halo, ($C_1$–$C_4$)alkyl, nitro, hydroxy, amino, mono- or di-substituted ($C_1$–$C_4$)alkylamino, ($C_1$–$C_4$)alkoxy, ($C_1$–$C_4$)alkylsulfonyl, cyano and carboxy; (heterocycle) methyl group said heterocycle selected from 4-(or 3-)imidazolyl, 4-(or 3-)oxazolyl, 3-(or 2-)indolyl, 2-(or 3-)furanyl, 2-(or 3-)thienyl, 2-(or 3-)pyrrolyl and 2-(or 3-)pyrazolyl; ($C_3$–$C_6$)cycloalkylmethyl group selected from (cyclopropyl)methyl, (cyclobutyl)methyl, (cyclopentyl)methyl and (cyclohexyl)methyl;

$R^2$ is selected from hydrogen and ($C_1$–$C_6$)alkyl selected from methyl, ethyl, propyl, isopropyl, butyl, isobutyl, pentyl and hexyl;

W is selected from amino; hydroxylamino; ($C_1$–$C_{12}$) straight or branched alkyl monosubstituted amino group substitution selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl, 1-methyl-1-ethylpropyl, heptyl, octyl, nonyl, decyl, undecyl and dodecyl and the diastereomers and enantiomers of said branched alkyl monosubstituted amino group; ($C_3$–$C_8$)cycloalkyl monosubstituted amino group substitution selected from cyclopropyl, trans-1,2-dimethylcyclopropyl, cis-1,2-dicyclopropyl, cyclobutyl, cyclopentyl, cyclohexyl, cycloheptyl, cyclooctyl, bicyclo [2.2.1]hept-2-yl, and bicyclo[2.2.2]oct-2-yl and the diastereomers and enantiomers of said ($C_3$–$C_8$)cycloalkyl monosubstituted amino group; [($C_4$–$C_{10}$)cycloalkyl] ($C_1$–$C_3$)alkyl monosubstituted amino group substitution selected from (cyclopropyl)-methyl, (cyclopropyl)ethyl, (cyclobutyl)methyl, (trans-2-methylcyclopropyl)methyl, and (cis-2-methylcyclobutyl)methyl; ($C_3$–$C_{10}$)alkenyl monosubstituted amino group substitution selected from allyl, 3-butenyl, 2-butenyl (cis or trans), 2-pentenyl, 4-octenyl, 2,3-dimethyl-2-butenyl, 3-methyl-2-butenyl 2-cyclopentenyl and 2-cyclohexenyl; ($C_6$–$C_{10}$)aryl monosubstituted amino group substitution selected from phenyl and naphthyl; ($C_7$–$C_{11}$)aralkylamino group selected from benzyl, 2-phenylethyl, 1-phenylethyl, 2-(naphthyl) methyl, 1-(naphthyl)methyl and phenylpropyl; straight or branched symmetrical disubstituted ($C_2$–$C_8$)alkylamino group substitution selected from dimethyl, diethyl, diisopropyl and di-n-propyl; symmetrical disubstituted ($C_3$–$C_{14}$)cycloalkylamino group substitution selected from dicyclopropyl, dicyclobutyl, dicyclopentyl, dicylohexyl and dicycloheptyl; straight or branched unsymmetrical disubstituted ($C_3$–$C_{14}$)alkylamino group wherein the total number of carbons in the substitution is not more than 14; unsymmetrical disubstituted ($C_4$–$C_{14}$) cycloalkylamino group wherein the total number of carbons in the substitution is not more than 14; ($C_2$–$C_8$) azacycloalkyl and substituted ($C_2$–$C_8$)azacycloalkyl group selected from aziridinyl, azetidinyl, pyrrolidinyl, piperidinyl, 4-methylpiperidinyl, 2-methylpyrrolidinyl, cis-3,4-dimethylpyrrolidinyl, trans-3,4-dimethylpyrrolidinyl, 2-azabicyclo[2.1.1]hex-2-yl, 5-azabicyclo[2.1.1]hex-5-yl, 2-azabicyclo[2.2.1]hept-2-yl, 7-azabicyclo[2.2.1]hept-7-yl, and 2-azabicyclo[2.2.2]oct-2-yl and the diastereomers and enantiomers of said ($C_2$–$C_8$)azacycloalkyl and substituted ($C_2$–$C_8$) azacycloalkyl group; 1-azaoxacycloalkyl group selected from morpholinyl and 1-aza-5-oxacycloheptane; substituted 1-azaoxacycloalkyl group selected from 2-($C_1$–$C_3$) alkylmorpholinyl, 2-($C_3$–$C_6$)cycloalkylmorpholinyl, 3-($C_1$–$C_3$)alkylisoxazolidinyl, tetrahydrooxazinyl and 3,4-dihydrooxazinyl; [1,n]-diazacycloalkyl and substituted [1,n]-diazacycloalkyl group selected from piperazinyl, 2-($C_1$–$C_4$)alkylpiperazinyl, 2-($C_3$–$C_6$) cycloalkylpiperazinyl, 4-($C_1$–$C_3$)alkylpiperazinyl, 2,4-dimethylpiperazinyl, 4-($C_1$–$C_3$)alkoxypiperazinyl, 4-($C_6$–$C_{10}$)-aryloxypiperazinyl, 4-hydroxypiperazinyl, 2,5-diaza-bicyclo[2.2.1]hept-2-yl, 2,5-diaza-5-methylbicyclo-[2.2.1]hept-2-yl, 2,3-diaza-3-methylbicyclo[2.2.2]-oct-2-yl, and 2,5-diaza-5,7-dimethylbicyclo[2.2.2]oct- 2-yl and the diastereomers or enantiomers of said [1,n]-diazacycloalkyl and substituted [1,n]-diazacycloalkyl group; 1-azathiacycloalkyl and substituted 1-azathiacycloalkyl group selected from thiomorpholinyl, 2-($C_1$–$C_3$)alkylthiomorpholinyl and 3-($C_3$–$C_6$)cycloalkylthiomorpholinyl; N-azolyl and substituted N-azolyl group selected from 1-imidazolyl, 2-($C_1$–$C_3$)alkyl-1-imidazolyl, 3-($C_1$–$C_3$)alkyl-1-imidazolyl, 1-pyrrolyl, 2-($C_1$–$C_3$)alkyl-1-pyrrolyl, 3-($C_1$–$C_3$)alkyl-1-pyrazolyl, 1-pyrazolyl, 3-($C_1$–$C_3$)alkyl-1-pyrazolyl, indolyl, 1-(1,2,3-triazolyl), 4-alkyl-1-(1,2,3-triazolyl), 5-($C_1$–$C_3$)alkyl-1-(1,2,3-triazolyl), 4-(1,2,4-triazolyl), 1-tetrazolyl, 2-tetrazolyl and benzimidazolyl; (heterocycle)amino group said heterocycle selected from 2- or 3-furanyl, 2- or 3-thienyl, 2-, 3- or 4-pyridyl, 2- or 5-pyridazinyl, 2-pyrazinyl, 2-(imidazolyl), (benzimidazolyl), and (benzothiazolyl) and substituted (heterocycle) amino group (substitution selected from straight or branched ($C_1$–$C_6$)alkyl); (heterocycle) methylamino group selected from 2- or 3-furylmethylamino, 2- or 3-thienylmethylamino, 2 -, 3 - or 4-pyridylmethylamino, 2 - or 5-pyridazinylmethylamino, 2-pyrazinylmethylamino, 2-(imidazolyl)methylamino, (benzimidazolyl) methylamino, and (benzothiazolyl)methylamino and substituted (heterocycle) methylamino group (substitution selected from straight or branched ($C_1$–$C_6$)alkyl); carboxy ($C_2$–$C_4$)alkylamino group selected from aminoacetic acid, α-aminopropionic acid, β-aminopropionic acid, α-butyric acid, and β-aminobutyric acid and the enantiomers of said carboxy($C_2$–$C_4$)alkylamino group; ($C_1$–$C_4$) alkoxycarbonylamino group selected from methoxycarbonylamino, ethoxycarbonylamino, allyloxycarbonylamino, propoxycarbonylamino, isoproproxycarbonylamino, 1,1-dimethylethoxycarbonylamino, n-butoxycarbonylamino, and 2-methylpropoxycarbonylamino; ($C_1$–$C_4$) alkoxyamino group selected from methoxyamino, ethoxyamino, n-propoxyamino, 1-methylethoxyamino, n-butoxyamino, 2 -methylpropoxyamino, and 1,1-dimethylethoxyamino; ($C_3$–$C_8$)cycloalkoxyamino group substitution selected from cyclopropoxy, trans-1,2-dimethylcyclo-propoxy, cis-1,2-dimethylcyclopropoxy, cyclobutoxy, cyclopentoxy, cyclohexoxy, cycloheptoxy, cyclooctoxy, bicyclo[2.2.1]hept-2-yloxy, and bicyclo [2.2.2]oct-2-yloxy and the diastereomers and enantiomers of said ($C_3$–$C_8$)cycloalkoxyamino group; ($C_6$–$C_{10}$) aryloxyamino group selected from phenoxyamino, 1-naphthyloxyamino and 2-naphthyloxyamino; ($C_7$–$C_{11}$) arylalkoxyamino group substitution selected from benzyloxy, 2-phenylethoxy, 1-phenylethoxy, 2-(naphthyl) methoxy, 1-(naphthyl)methoxy and phenylpropoxy; or $R^1$ and W taken together are —$CH_2(CH_2)_nCH_2N$—, wherein n=1–3;

and the pharmacologically acceptable organic and inorganic salts or metal complexes.

Particularly preferred compounds are compounds according to the above formula I, wherein:

R is selected from methylene, α-$CH_3$ and β-$CH_3$;

$R^1$ is selected from hydrogen; straight or branched ($C_1$–$C_8$) alkyl group selected from methyl, ethyl, propyl, isopropyl, butyl, isobutyl, pentyl, hexyl, heptyl and octyl; straight or branched ($C_1$–$C_8$)alkyl group optionally substituted with α-mercapto, α-hydroxy, carboxyl, carboxamido, or amino; ($C_6$–$C_{10}$)aryl group selected from phenyl, α-naphthyl and β-naphthyl; ($C_7$–$C_9$)aralkyl group selected from benzyl, 1-phenylethyl, 2-phenylethyl and phenylpropyl; (heterocycle)methyl group said hetrocycle selected from 4-(or 3-)imidazolyl, 4-(or 3-)oxazolyl, 3-(or 2-)indolyl, 2-(or 3-)furanyl and 2-(or 3-)thienyl; ($C_3$–$C_6$) cycloalkylmethyl group selected from (cyclopropyl) methyl, (cyclobutyl)methyl, (cyclopentyl)methyl and (cyclohexyl)methyl;

$R^2$ is selected from hydrogen and ($C_1$–$C_6$)alkyl selected from methyl, ethyl, propyl, isopropyl, butyl, isobutyl, pentyl and hexyl;

W is selected from amino; ($C_1$–$C_{12}$) straight or branched alkyl monosubstituted amino group substitution selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl, 1-methyl-1-ethylpropyl, heptyl, octyl, nonyl and decyl and the diastereomers and enantiomers of said branched alkyl monosubstituted amino group; ($C_3$–$C_8$)cycloalkyl monosubstituted amino group substitution selected from cyclopropyl, trans-1,2-dimethylcyclopropyl, cis-1,2-dimethylcyclopropyl, cyclobutyl, cyclopentyl, cyclohexyl, cycloheptyl and cyclooctyl and the diastereomers and enantiomers of said ($C_3$–$C_8$)cycloalkyl monosubstituted amino group; [($C_4$–$C_{10}$)cycloalkyl] ($C_1$–$C_2$) alkyl monosubstituted amino group substitution selected from (cyclopropyl)methyl, (cyclopropyl)ethyl and (cyclobutyl)methyl; ($C_3$–$C_{10}$)alkenyl monosubstituted amino group substitution selected from allyl, 3-butenyl, 2-butenyl (cis or trans), 2-pentenyl, 4-octenyl, 2,3-dimethyl-2-butenyl, 3-methyl-2-butenyl 2-cyclopentenyl and 2-cyclohexenyl; ($C_7$–$C_{10}$)aralkylamino group selected from benzyl, 2-phenylethyl, 1-phenylethyl, 2-(naphthyl)methyl, 1-(naphthyl)methyl and phenylpropyl; straight or branched symmetrical disubstituted ($C_2$–$C_8$)alkylamino group substitution selected from dimethyl, diethyl, diisopropyl and di-n-propyl; straight or branched unsymmetrical disubstituted ($C_3$-$C_{14}$) alkylamino group wherein the total number of carbons in the substitution is not more than 14; unsymmetrical disubstituted ($C_4$-$C_{14}$)cycloalkylamino group wherein the total number of carbons in the substitution is not more than 14; ($C_2$-$C_8$)azacycloalkyl and substituted ($C_2$-$C_8$) azacycloalkyl group selected from aziridinyl, azetidinyl, pyrrolidinyl, piperidinyl, 4-methylpiperidinyl, 2-methylpyrrolidinyl, cis-3,4-dimethylpyrrolidinyl, and trans-3,4-dimethylpyrrolidinyl and the diastereomers and enantiomers of said ($C_2$-$C_8$)azacycloalkyl and substituted ($C_2$-$C_8$)azacycloalkyl group; 1-azaoxacycloalkyl group selected from morpholinyl and 1-aza-5-oxacycloheptane; substituted 1-azaoxacycloalkyl group selected from 2-($C_1$-$C_3$)alkylmorpholinyl, 3-($C_1$-$C_3$) alkylisooxazolidinyl and tetrahydrooxazinyl; [1,n]-diazacycloalkyl and substituted [1,n]-diazacycloalkyl group selected from piperazinyl, 2-($C_1$-$C_3$) alkylpiperazinyl, 4-($C_1$-$C_3$)alkylpiperazinyl, 2,4-dimethylpiperazinyl, 4-hydroxypiperazinyl, 2,5-diazabicyclo[2.2.1]hept-2-yl, 2,5-diaza-5-methylbicyclo [2.2.1]hept-2-yl, and 2,3-diaza-3-methylbicyclo[2.2.2] oct-2-yl, the diastereomers or enantiomers of said [1,n]-diazacycloalkyl and substituted [1,n]-diazacycloalkyl group; 1-azathiacycloalkyl and substituted 1-azathiacycloalkyl group selected from thiomorpholinyl and 2-($C_1$-$C_3$)alkylthiomorpholinyl; N-azolyl and substituted N-azolyl group selected from 1-imidazolyl, 2-($C_1$-$C_3$)alkyl-1-imidazolyl, 3-($C_1$-$C_3$)alkyl-1-imidazolyl, 1-pyrrolyl, 2-($C_1$-$C_3$)alkyl-1-pyrrolyl, 3-($C_1$-$C_3$)alkyl-1-pyrrolyl, 1-pyrazolyl, 3-($C_1$-$C_3$)alkyl-1-pyrazolyl, indolyl, 1-(1,2,3-triazolyl), 4-($C_1$-$C_3$)alkyl-1-(1,2,3-triazolyl), 5-($C_1$-$C_3$)alkyl-1-(1,2,3-triazolyl) and 4-(1,2,4-triazolyl; (heterocycle)methylamino group selected from 2- or 3-furylmethylamino, 2- or 3-thienylmethylamino, 2-, 3- or 4-pyridylmethylamino, 2- or 5-pyridazinylmethylamino, 2-pyrazinylmethylamino, 2-(imidazolyl)methylamino, (benzimidazolyl) methylamino, and (benzothiazolyl)methylamino and substituted (heterocycle)methylamino group (substitution selected from straight or branched ($C_1$-$C_6$)alkyl); carboxy ($C_2$-$C_4$)alkylamino group selected from aminoacetic acid, α-aminopropionic acid, β-aminopropionic acid, α-butyric acid, and β-aminobutyric acid and the enantiomers of said carboxy($C_2$-$C_4$)alkylamino group; ($C_1$-$C_4$) alkoxycarbonylamino group selected from methoxycarbonylamino, ethoxycarbonylamino, allyloxycarbonylamino, propoxycarbonylamino, isoproproxycarbonylamino, 1,1-dimethylethoxycarbonylamino, n-butoxycarbonylamino, and 2-methylpropoxycarbonylamino, ($C_1$-$C_4$) alkoxyamino group substitution selected from methoxy, ethoxy, n-propoxy, 1-methylethoxy, n-butoxy, 2-methylpropoxy, and 1,1-dimethylethoxy; ($C_7$-$C_{11}$) arylalkoxyamino group substitution selected from benzyoxy, 2-phenylethoxy, 1-phenylethoxy, 2-(naphthyl) methoxy, 1-(naphthyl)methoxy and phenylpropoxy; or $R^1$ and W taken together are —$CH_2(CH_2)_nCH_2NH$—, wherein n=1–3;
and the pharmacologically acceptable organic and inorganic salts or metal complexes.

Compounds of special interest are compounds according to the above formula I and II wherein:

R is selected from α-$CH_3$;

$R^1$ is selected from hydrogen; straight or branched ($C_1$-$C_4$) alkyl group selected from methyl, ethyl, propyl and butyl;

straight or branched ($C_1$-$C_4$)alkyl group optionally substituted with amino; (heterocyclo)methyl group said heterocycle selected from imidazolyl and 3-indolyl; ($C_5$-$C_6$) cycloalkylmethyl group selected from (cyclopentyl) methyl and (cyclohexyl) methyl; ($C_2$-$C_4$) carboxamidoalkyl group selected from carboxamidomethyl and carboxamidoethyl;

$R^2$ is selected from hydrogen and ($C_1$-$C_2$)alkyl selected from methyl and ethyl;

W is selected from amino; ($C_1$-$C_8$) straight or branched alkyl monosubstituted amino group substitution selected from methyl, ethyl, n-propyl, 1-methylethyl, n-butyl, 1-methylpropyl, 2-methylpropyl, n-hexyl and n-octyl; ($C_3$-$C_6$)cycloalkyl monosubstituted amino group substitution selected from cyclopropyl, cyclopentyl and cyclohexyl; [($C_4$-$C_5$)cycloalkyl] ($C_1$-$C_2$)alkyl monosubstituted amino group substitution selected from (cyclopropyl)methyl and (cyclopropyl)ethyl; ($C_3$-$C_4$) alkenyl monosubstituted amino group substitution selected from allyl and 3-butenyl; ($C_7$-$C_{10}$)aralkylamino group selected from benzyl, 2-phenylethyl and 1-phenylethyl; straight or branched symmetrical disubstituted ($C_2$-$C_4$)alkylamino group substitution selected from dimethyl and diethyl; straight or branched unsymmetrical disubstituted ($C_3$)alkylamino group substitution selected from methyl(ethyl); ($C_2$-$C_5$)azacycloalkyl group selected from pyrrolidinyl and piperidinyl; 1-azaoxacycloalkyl group selected from morpholinyl; substituted-1-azaoxacycloalkyl group selected from 2-($C_1$-$C_3$) alkylmorpholinyl; [1,n]-diazacycloalkyl and substituted [1,n]-diazacycloalkyl group selected from piperazinyl, 2-($C_1$-$C_3$)alkylpiperazinyl, 4-($C_1$-$C_3$)alkylpiperazinyl, and 2,5-diaza-5-methylbicyclo[2.2.1]hept-2-yl and the diastereomers and enantiomers of said [1,n]-diazacycloalkyl and substituted [1,n]-diazacycloalkyl group; 1-azathiacycloalkyl and substituted 1-azathiacycloalkyl group selected from thiomorpholinyl and 2-($C_1$-$C_3$)alkylthiomorpholinyl; N-azolyl group selected from 1-imidazolyl; (heterocycle)methylamino group selected from 2- or 3-thienylmethylamino and 2-, 3- or 4-pyridylmethylamino; ($C_1$-$C_4$) alkoxycarbonylamino group substitution selected from methoxycarbonylamino, ethoxycarbonylamino, and 1,1-dimethylethoxycarbonylamino; or $R^1$ and W taken together are —$CH_2CH_2CH_2NH$—;

and the pharmacologically acceptable organic and inorganic salts or metal complexes.

Also included in the present invention are compounds useful as intermediates for producing the above compounds of formula I. Such intermediate include those having the formula II:

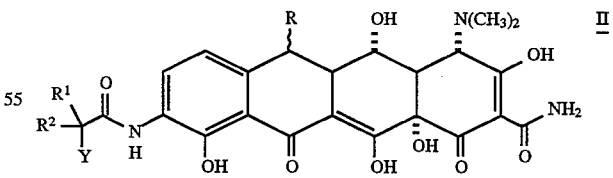

wherein:

Y is selected from $(CH_2)_nX$, n=0–5, X is halogen selected from bromine, chlorine, fluorine and iodine; alternatively, X is a protected amino selected from trifluoroacetylamino, ($C_1$-$C_4$)alkoxycarbonylamino selected from t-butoxycarbonylamino, methoxycarbonylamino, ethoxycarbonylamino, allyloxycarbonylamino and 1,1,1-trichloroethoxycarbonylamino, ($C_7$-$C_{14}$)arylalkoxycarbonylamino selected from benzyloxycarbonylamino, naphthylmethoxycarbonylamino, 9-fluorenylmethoxycarbonylamino, p-methoxybenzyloxycarbonylamino, and p-nitrobenzyloxycarbonylamino, ($C_7$–$C_{23}$) aralkylamino selected from benzylamine, p-methoxybenzylamine, p-nitrobenzylamine, tritylamine and 4-methoxytritylamine;

R is selected from methylene, α-$CH_3$ and β-$CH_3$;

$R^1$ is selected from hydrogen; straight or branched ($C_1$–$C_8$) alkyl group selected from methyl, ethyl, propyl, isopropyl, butyl, isobutyl, pentyl, hexyl, heptyl and octyl; straight or branched ($C_1$–$C_8$)alkyl group optionally substituted with α-mercapto, α-hydroxy, carboxyl, carboxamido, amino, guanidino or amidino; ($C_6$–$C_{10}$)aryl group selected from phenyl, α-naphthyl and β-naphthyl; substituted ($C_6$–$C_{10}$)aryl group substitution selected from hydroxy, halogen, ($C_1$–$C_4$)alkoxy, trihalo($C_1$–$C_3$)alkyl, nitro, amino, cyano, ($C_1$–$C_4$)alkoxycarbonyl, ($C_1$–$C_3$) alkylamino and carboxy; ($C_7$–$C_9$)aralkyl group selected from benzyl, 1-phenylethyl, 2-phenylethyl and phenylpropyl; substituted ($C_7$–$C_9$)aralkyl group substitution selected from halo, ($C_1$–$C_4$)alkyl, nitro, hydroxy, amino, mono- or di-substituted ($C_1$–$C_4$)alkylamino, ($C_1$–$C_4$) alkoxy, ($C_1$–$C_4$)alkylsulfonyl, cyano and carboxy; (heterocycle)methyl group said heterocycle selected from 4-(or 3-)imidazolyl, 4-(or 3-)oxazolyl, 3-(or 2-)indolyl, 2-(or 3-)furanyl, 2-(or 3-)thienyl, 2-(or 3-) pyrrolyl, 2-(or 3-) pyrazolyl, 4-(1,2,3-triazolyl) and benzimidazolyl; ($C_3$–$C_6$)cycloalkylmethyl group selected from (cyclopropyl)methyl, (cyclobutyl)methyl, (cyclopentyl) methyl and (cyclohexyl)methyl;

$R^2$ is selected from hydrogen and ($C_1$–$C_6$)alkyl selected from methyl, ethyl, propyl, isopropyl, butyl, isobutyl, pentyl and hexyl. It will be appreciated that when $R^1$ does not equal $R^2$ the stereochemistry of the asymmetric carbon (i.e. the carbon bearing the W substituent) maybe be either the racemate (DL) or the individual enantiomers (n or D); and the pharmacologically acceptable organic and inorganic salts and metal complexes.

Preferred compounds are compounds according to the above formula II wherein:

Y is selected from $(CH_2)_nX$, n=0–5, X is halogen selected from bromine, chlorine, fluorine and iodine; alternatively, X is a protected amino selected from trifluoroacetylamino, ($C_1$–$C_4$)alkoxycarbonylamino selected from t-butoxycarbonylamino, methoxycarbonylamino, ethoxycarbonylamino, allyloxycarbonylamino and 1,1,1-trichloroethoxycarbonylamino, ($C_7$–$C_{14}$)arylalkoxycarbonylamino selected from benzyloxycarbonylamino, naphthylmethoxycarbonylamino, 9-fluorenylmethoxycarbonylamino, p-methoxybenzyloxycarbonylamino, and p-nitrobenzyloxycarbonylamino, ($C_7$–$C_{23}$) aralkylamino selected from benzylamine, p-methoxybenzylamine, p-nitrobenzylamine, tritylamine and 4-methoxytritylamine;

R is selected from methylene, α-$CH_3$ and β-$CH_3$;

$R^1$ is selected from hydrogen; straight or branched ($C_1$–$C_8$) alkyl group selected from methyl, ethyl, propyl, isopropyl, butyl, isobutyl, pentyl, hexyl, heptyl and octyl; straight or branched ($C_1$–$C_8$)alkyl group optionally substituted with α-mercapto, α-hydroxy, carboxyl, carboxamido, amino, guanidino or amidino; ($C_6$–$C_{10}$)aryl group selected from phenyl, α-naphthyl and β-naphthyl; ($C_7$–$C_9$)aralkyl group selected from benzyl, 1-phenylethyl, 2-phenylethyl and phenylpropyl; substituted($C_7$–$C_9$)aralkyl group substitution selected from halo, ($C_1$–$C_4$)alkyl, nitro, hydroxy, amino, mono- or di-substituted ($C_1$–$C_4$)alkylamino, ($C_1$–$C_4$)alkoxy, ($C_1$–$C_4$)alkylsulfonyl, cyano and carboxy;

$R^2$ is selected from hydrogen and ($C_1$–$C_6$)alkyl selected from methyl, ethyl, propyl, isopropyl, butyl, isobutyl, pentyl and hexyl; and the pharmacologically acceptable organic and inorganic salts and metal complexes.

Particularly preferred compounds are compounds according to the above formula II wherein:

Y is selected from $(CH_2)_nX$, n=0–5, X is halogen selected from bromine, chlorine, fluorine and iodine; alternatively, X is a protected amino selected from trifluoroacetylamino, ($C_3$–$C_4$) alkoxycarbonylamino selected from t-butoxycarbonylamino, allyloxycarbonylamino and 1,1,1-trichloroethoxycarbonylamino, ($C_7$–$C_{14}$)arylalkoxycarbonylamino selected from benzyloxycarbonylamino, and 9-fluorenylmethoxycarbonylamino], ($C_7$–$C_{23}$) arylalkylamino selected from benzylamine, and tritylamine;

R is selected from methylene, α-$CH_3$ and β-$CH_3$;

$R^1$ is selected from hydrogen; straight or branched ($C_1$–$C_8$) alkyl group selected from methyl, ethyl, propyl, isopropyl, butyl, isobutyl, pentyl, hexyl, heptyl and octyl; straight or branched ($C_1$–$C_8$)alkyl group optionally substituted with α-mercapto, α-hydroxy, carboxyl, carboxamido; ($C_6$–$C_{10}$)aryl group selected from phenyl, α-naphthyl and β-naphthyl; ($C_7$–$C_9$)aralkyl group selected from benzyl, 1-phenylethyl, 2-phenylethyl and phenylpropyl;

$R^2$ is selected from hydrogen and ($C_1$–$C_6$)alkyl selected from methyl, ethyl, propyl, isopropyl, butyl, isobutyl, pentyl and hexyl; and the pharmacologically acceptable organic and inorganic salts and metal complexes.

Compounds of special interest are compounds according to the above formula II wherein:

Y is selected from $(CH_2)_nX$, n=0–5, X is halogen selected from bromine, chlorine, fluorine and iodine; alternatively, X is a protected amino selected from triluoroacetylamino, ($C_3$–$C_4$)alkoxycarbonylamino selected from t-butoxycarbonylamino and allyloxycarbonylamino], ($C_7$–$C_{14}$)arylalkoxycarbonylamino selected from benzyloxycarbonylamino, and 9-fluorenylmethoxycarbonylamino], ($C_7$–$C_{23}$) arylalkylamino [selected from benzylamine and tritylamine];

R is selected from α-$CH_3$;

$R^1$ is selected from hydrogen; straight or branched ($C_1$–$C_4$) alkyl group selected from methyl, ethyl, propyl and butyl; straight or branched ($C_1$–$C_4$)alkyl group optionally substituted with amino; (heterocyclo)methyl group said heterocycle selected from imidazolyl and 3-indolyl; ($C_5$–$C_6$) cycloalkylmethyl group selected from (cyclopentyl) methyl and (cyclohexyl)methyl; ($C_2$–$C_4$) carboxamidoalkyl group selected from carboxamidomethyl and carboxamidoethyl;

$R^2$ is selected from hydrogen and ($C_1$–$C_2$)alkyl selected from methyl and ethyl; and the pharmacologically acceptable organic and inorganic salts and metal complexes.

DESCRIPTION OF THE PREFERRED EMBODIMENTS

The novel compounds of the present invention may be readily prepared in accordance with the following schemes.

Scheme I

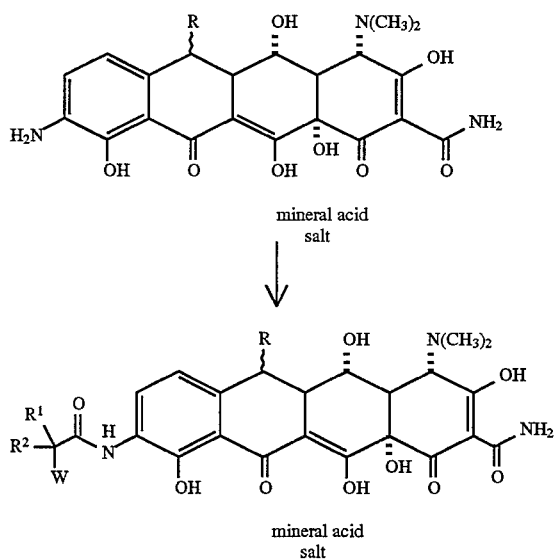

The 9-[(substituted glycyl)amido]-6-(substituted)-5-hydroxy-6-deoxytetracyclines, or mineral acid salts, can be made by the procedure described in scheme I. In accordance with scheme I, 9-amino-6-(substituted)-5-hydroxy-6-deoxytetracycline or its mineral acid salt, 1, is dissolved in a mixture of 1,3-dimethyl-3,4,5,6-tetrahydro-2(1H) pyrimidone and acetonitrile or equivalent solvents. Sodium carbonate is added and the mixture is stirred for 5 minutes. An acid chloride, acid anhydride or suitably activated acylation reagent of the formula:

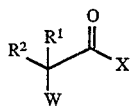

wherein X=suitable leaving group and $R^1$, $R^2$, and W have been described hereinabove, is added and the reaction is stirred at room temperature for from 0.5–2 hours to give the corresponding 9-[(substituted glycyl)amido]-6-(substituted)-5-hydroxy-6-deoxytetracycline, or its mineral acid salt 3.

Scheme II

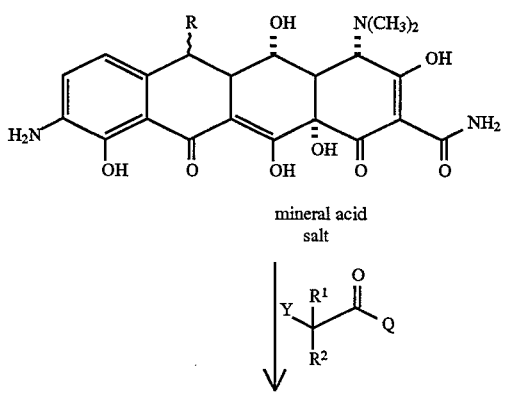

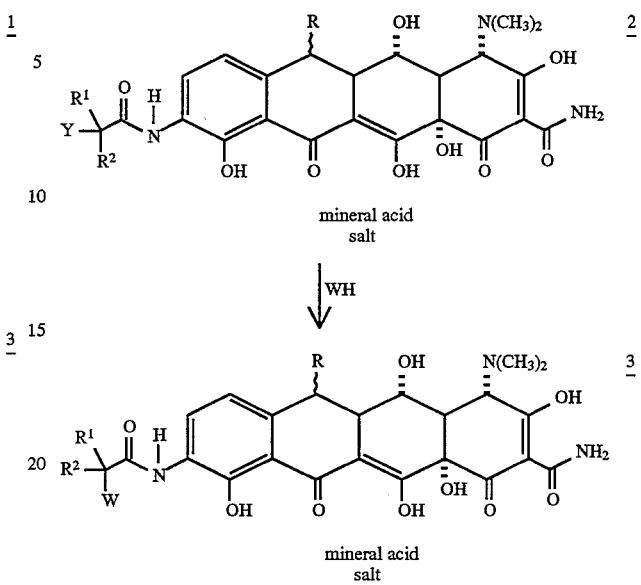

The second method for producing 9-[(substituted glycyl) amido]-6-(substituted)-5-hydroxy-6-deoxytetracyclines or its mineral acid salt 3, is shown in scheme II. This method uses common intermediates which are easily prepared by reacting commercially available haloacyl halides, anhydrides or suitably activated haloacylating agents of the formula:

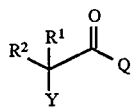

wherein Y, $R^1$ and $R^2$ are as defined hereinabove and Q is halogen selected from bromine, chlorine, iodine, fluorine or suitable leaving group; with 9-amino-6-(substituted)-5-hydroxy-6-deoxytetracyclines, or its mineral acid salt 1, to give straight or branched 9-[(haloacyl)amido]-6-(substituted)-5-hydroxy-6-deoxytetracyclines or its mineral acid salt, 2, in almost quantitative yield. The above intermediates, straight or branched 9-[(haloacyl)amido]-6-(substituted)-5-hydroxy-6-deoxytetracyclines or its mineral acid salt 2, react with a wide variety of nucleophiles, especially amines, having the formula WH, wherein W is as defined hereinabove to give the new 9-[(substituted glycyl) amido]-6-(substituted)-5-hydroxy-6-deoxytetracyclines or mineral acid salt 3 of the present invention.

In accordance with Scheme II, 9-amino-6-(substituted)-5-hydroxy-6-deoxytetracycline or its mineral acid salt, 1, is mixed with a) a polar-aprotic or protic (low temp.) solvent such as 1,3-dimethyl-3,4,5,6-tetrahydro-2(1H)-pyrimidone, herein after called DMPU, hexamethylphosphoramide herein after called HMPA, dimethylformamide, dimethylacetamide, N-methylpyrrolidone, 1,2-dimethoxyethane, water or equivalent thereof;

b) an inert solvent such as acetonitrile, methylene chloride, tetrahydrofuran chloroform, carbon tetrachloride, 1,2-dichloroethane, tetrachloroethane, diethyl ether, t-butyl methyl ether, isopropyl ether or equivalent thereof;

c) a base such as sodium carbonate, sodium bicarbonate, sodium acetate, potassium carbonate, potassium bicarbonate, triethylamine, cesium carbonate, lithium carbonate or bicarbonate equivalents; and d) a straight or branched haloacyl halide, anhydride or suitably activated haloacylating agent of the formula:

Academic Press, 1991]. It is well known to one skilled in the art that the appropriate nitrogen protection and deprotection scheme is chosen based on chemical and physical stability.

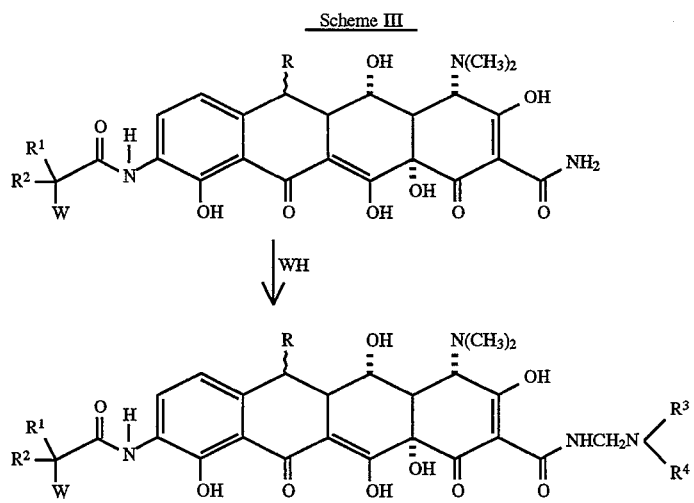

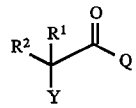

wherein Y, $R^1$, $R^2$ and Q are as defined hereinabove such as bromoacetyl bromide, (bromoacetic anhydride, chloroacetyl chloride (chloroacetic anhydride) or 2-bromopropionyl bromide or equivalent thereof; the halo, Y, and halide, Q, in the haloacyl halide can be the same or different halogen and is selected from bromine, chlorine, iodine and fluorine; Y is $(CH_2)_n X$, n=0–5, X is halogen;

e) for 0.5 to 5 hours at room temperature to the reflux temperature of the reaction; to form the corresponding 9-[(haloacyl)amido]-6-(substituted)-5-hydroxy-6-deoxytetracycline, 2, or its mineral acid salt.

The intermediate, 9-[(haloacyl)amido]-6-(substituted)-5-hydroxy-6-deoxytetracycline or mineral acid salt 2, is treated, under an inert atmosphere of helium, argon or nitrogen, with a) a nucleophile WH such as an amine or substituted amine or equivalent for example methylamine, dimethylamine, ethylamine, n-butylamine, propylamine or n-hexylamine;

b) a polar-aprotic or protic solvent such as DMPU, HMPA, dimethylformamide, dimethylacetamide, N-methylpyrrolidone, 1,2-dimethoxyethane, water or equivalent;

c) for from 0.5–2 hours at room temperature or under reflux temperature to produce the desired 9-[(substituted glycyl)amido]-6-(substituted)-5-hydroxy-6-deoxytetracycline, 3, or its mineral acid salt.

Alternatively, the intermediate, 9-[(protected aminoacyl) amido]-6-(substituted)-5-hydroxy-6-deoxytetracycline (Y=protected amino group), is treated under an inert atmosphere of helium, argon or nitrogen with an appropriate nitrogen deprotection reagent using methods known to those skilled in the art [(a) Richard C. Larock, Comprehensive Organic Transformations, VCH Publishers, 1989; (b) Theodora Greene, Protecting Groups in Organic Synthesis, In accordance with Scheme III, compounds of formula 3 are N-alkylated in the presence of formaldehyde and either a primary amine such as methylamine, ethylamine, benzylamine, methyl glycinate, (L or D)alanine, (L or D)lysine or their substituted congeners; or a secondary amine such as morpholine, pyrrolidine, piperidine or their substituted congeners to give the corresponding Mannich base adduct, 4.

The 9-[(substituted glycyl)amido]-6-(substituted)-5-hydroxy-6-deoxytetracyclines may be obtained as metal complexes such as aluminum, calcium, iron, magnesium, manganese and complex salts; inorganic and organic salts and corresponding Mannich base adducts using methods known to those skilled in the art (Richard C. Larock, Comprehensive Organic Transformations, VCH Publishers, 411–415, 1989). It is well known to one skilled in the art that an appropriate salt form is chosen based on physical and chemical stability, flowability, hygroscopicity and solubility. Preferably, the 9-[(substituted glycyl)amido]-6-(substituted)-5-hydroxy-6-deoxytetracyclines are obtained as inorganic salt such as hydrochloric, hydrobromic, hydroiodic, phosphoric, nitric or sulfate; or organic salt such as acetate, benzoate, citrate, cysteine or other amino acids, fumarate, glycolate, maleate, succinate, tartrate, alkylsulfonate or arylsulfonate. Depending on the stoichiometry of the acids used, the salt formation occurs with the C(4)-dimethylamino group (1 equivalent of acid) or with both the C(4)-dimethylamino group and the W group (2 equivalents of acid). The salts are preferred for oral and parenteral administration.

Some of the compounds of the hereinbefore described Schemes have centers of asymmetry at the carbon bearing the W substituent. The compounds may, therefore, exist in at least two (2) stereoisomeric forms. The present invention encompasses the racemic mixture of stereo isomers as well as all stereoisomers of the compounds whether free from other stereoisomers or admixed with stereoisomers in any proportion of enantiomers. The absolute configuration of any compound may be determined by conventional X-ray crystallography.

The stereochemistry centers on the tetracycline unit (i.e. C-4, C-4a, C-5, C-5a, C-6 and C-12a) remain intact throughout the reaction sequences.

BIOLOGICAL ACTIVITY

Method for in Vitro Antibacterial Evaluation (Table 1)

The minimum inhibitory concentration (MIC), the lowest concentration of the antibiotic which inhibits growth to the test organism, is determined by the agar dilution method using Muller-Hinton II agar (Baltimore Biological Laboratories). An inoculum density of $1-5\times10^5$ CFU/ml and a range of antibiotic concentrations (32–0.004 μg/ml) is used. The plates are incubated for 18 hours at 35° C. in a forced air incubator. The test organisms comprise strains that are sensitive to tetracycline and genetically defined strains that are resistant to tetracycline, due to inability to bind to bacterial ribosomes (tetM) or by a tetK encoded membrane protein which confers tetracycline resistance by energy-dependent efflux of the antibiotic from the cell.

Testing Results

The claimed compounds exhibited good in vitro activity against a spectrum of doxycycline-sensitive and doxycycline-resistant Gram-positive and Gram-negative bacteria (Table 1). Notably, compounds A–D, compared to deoxycycline, exhibited excellent in vitro activity against strains containing the two major resistance determinants: efflux, as represented by tetB and tetD (*E. coli* UBMS 88-1, *E. coli* MC4100 and *E. coli* J3272) and ribosomal protection, as represented by *S. aureus* UBMS 90-1 and UBMS 90-2 and *E. coli* UMBS 89-1 and 90-4. These compounds showed improved activity against *Enterococcus* and comparable activity to doxycycline against sensitive strains. Compounds E–F exhibited similar activity against deoxycycline-resistant, both efflux and ribosomal protection mechanisms, and deoxycycline-susceptible strains. Compounds G–H showed similar activity against doxycycline susceptible *S. aureus* strains and doxycycline-resistant (both efflux and ribosomal resistant) strains. Compounds I–J had similar activity against doxycycline-sensitive strains and strains resistant to doxycycline due to ribosomal protection, but were less effective against strains carrying the efflux (tetK) resistance mechanism.

As can be seen from Table 1, compounds of the invention can be used to prevent or control important mammalian and veterinary diseases such as diarrhea, urinary tract infections, infections of skin and skin structure, ear, nose and throat infections, wound infections, mastitis and the like.

Thus, the improved efficacy of 9-[(N,N-dimethylglycyl)amido]-6-(substituted)-5-hydroxy-6-deoxytetracycline is demonstrated by the in vitro activity against isogenic strains into which the resistance determinants, such as tetM, are cloned (Table 1).

LEGEND FOR COMPOUNDS

| Compound | Name |
| --- | --- |
| Doxycycline | [4S-(4alpha,12aalpha)]-4-(Dimethylamino)-1,4,4a,5,5a,6,11,12a-octahydro-3,5,10,12,12a-pentahydroxy-6-methyl-1,11-dioxo-2-naphthacenecarboxamide |
| A | [4S-(4alpha,12aalpha)]-4-(Dimethylamino)-9-[[(dimethylamino)acetyl]amino]-1,4,4a,5,5a,6,11,12a-octahydro-3,5,10,12,12a-pentahydroxy-6-methyl-1,11-dioxo-2-naphthacenecarboxamide |
| B | [4S-(4alpha,12aalpha)]-4-(Dimethylamino)-9-[(L-leucyl)amino]-1,4,4a,5,5a,6,11,12a-octahydro-3,5,10,12,12a-pentahydroxy-6-methyl-1,11-dioxo-2-naphthacenecarboxamide |
| C | [4S-(4alpha,12aalpha)]-4-(Dimethylamino)-9-[(L-phenylalanyl)amino]-1,4,4a,5,5a,6,11,12a-octahydro-3,5,10,12,12a-pentahydroxy-6-methyl-1,11-dioxo-2-naphthacenecarboxamide |
| D | [4S-(4alpha,12aalpha)]-4-(Dimethylamino)-9-[(D-phenylalanyl)amino]-1,4,4a,5,5a,6,11,12a-octahydro-3,5,10,12,12a-pentahydroxy-6-methyl-1,11-dioxo-2-naphthacenecarboxamide |
| E | [4S-(4alpha,12aalpha)]-4-(Dimethylamino)-9-[[L-β-(cyclohexyl)alanyl]amino]-1,4,4a,5,5a,6,11,12a-octahydro-3,5,10,12,12a-pentahydroxy-6-methyl-1,11-dioxo-2-naphthacenecarboxamide |
| F | [4S-(4alpha,12aalpha)]-4-(Dimethylamino)-9-[(L-prolyl)amino]-1,4,4a,5,5a,6,11,12a-octahydro-3,5,10,12,12a-pentahydroxy-6-methyl-1,11-dioxo-2-naphthacenecarboxamide |
| G | [4S-(4alpha,12aalpha)]-4-(Dimethylamino)-9-[(L-N,N-dimethylphenylalanyl)amino]-1,4,4a,5,5a,6,11,12a-octahydro-3,5,10,12,12a-pentahydroxy-6-methyl-1,11-dioxo-2-naphthacenecarboxamide |
| H | [4S-(4alpha,12aalpha)]-4-(Dimethylamino)-9-[(L-N-methylleucyl)amino]-1,4,4a,5,5a,6,11,12a-octahydro-3,5,10,12,12a-pentahydroxy-6-methyl-1,11-dioxo-2-naphthacenecarboxamide |
| I | [4S-(4alpha,12aalpha)]-4-(Dimethylamino)-9-[(L-tryptophanyl)amino]-1,4,4a,5,5a,6,11,12a-octahydro-3,5,10,12,12a-pentahydroxy-6-methyl-1,11-dioxo-2-naphthacenecarboxamide |
| J | [4S-(4alpha,12aalpha)]-4-(Dimethylamino)-9-[L-tyrosyl)amino]-1,4,4a,5,5a,6,11,12a-octahydro-3,5,10,12,12a-pentahydroxy-6-methyl-1,11-dioxo-2-naphthacenecarboxamide |
| K | [4S-(4alpha,12aalpha)]-4-(Dimethylamino)-9-[(L-glutaminyl)amino]-1,4,4a,5,5a,6,11,12,a-octahydro-3,5,10,12,12a-pentahydroxy-6-methyl-1,11-dioxo-2-naphthacenecarboxamide |
| L | [4S-(4alpha,12aalpha)]-4-(Dimethylamino)-9-[(L-glycyl)amino]-1,4,4a,5,5a,6,11,12a-octahydro-3,5,10,12,12a-pentahydroxy-6-methyl-1,11-dioxo-2-naphthacenecarboxamide |
| M | [4S-(4alpha,12aalpha)]-4-(Dimethylamino)-9-[(bromoacetyl)amino]-1,4,4a,5,5a,6,11,12a-octahydro-3,5,10,12,12a-pentahydroxy-6-methyl-1,11-dioxo-2-naphthacenecarboxamide |
| N | [4S-(4alpha,12aalpha)]-4-(Dimethylamino)-9-[(L-lysyl)amino]-1,4,4a,5,5a,6,11,12a-octahydro-3,5,10,12,12a-pentahydroxy-6-methyl-1,11-dioxo-2-naphthacenecarboxamide |

TABLE 1

Antimicrobial Activity of 9-(α-Aminoacyl)-6-(substituted)-5-hydroxy-6-deoxytetracyclines

| ORGANISM | Doxycycline | A | B | C | D | E | F | G |
|---|---|---|---|---|---|---|---|---|
| E. coli UBMS 88-1 (tetB) | 32.00 | 1.00 | 2.00 | 4.00 | 4.00 | 8.00 | 4.00 | 32.00 |
| E. coli MC4100 (tet-sensitive) | 0.25 | 0.25 | 0.50 | 0.50 | 1.00 | 2.00 | 1.00 | 8.00 |
| E. coli PRP1 (tetA) | 8.00 | 4.00 | 16.00 | 16.00 | 8.00 | 8.00 | 16.00 | 16.00 |
| E. coli MC4100 (TN10WT) | >32.00 | 1.00 | 2.00 | 4.00 | 4.00 | 4.00 | 4.00 | >32.00 |
| E. coli J3272 (tetC) | 8.00 | 8.00 | 4.00 | 8.00 | 4.00 | 8.00 | 8.00 | 32.00 |
| E. coli UBMS 89-1 (tetM) | 16.00 | 0.50 | 1.00 | 2.00 | 4.00 | 2.00 | 2.00 | 8.00 |
| E. coli UBMS 89-2 (tet-sensitive) | 2.00 | 0.50 | 1.00 | 4.00 | 4.00 | 8.00 | 2.00 | 32.00 |
| E. coli J2175 (par J2445) | 2.00 | 0.50 | 2.00 | 4.00 | 4.00 | 4.00 | 2.00 | 32.00 |
| E. coli J2445 (IMP mut) | 0.25 | 0.12 | 0.50 | 0.50 | 0.50 | 1.00 | 1.00 | 2.00 |
| E. coli UBMS 90-4 (tetM) | 32.00 | 0.25 | 1.00 | 2.00 | 2.00 | 4.00 | 2.00 | 16.00 |
| E. coli UBMS 90-5 K-12 | 1.00 | 0.50 | 1.00 | 4.00 | 4.00 | 4.00 | 2.00 | 32.00 |
| E. coli #311 MP (Mino-sensitive) | 1.00 | 0.50 | 1.00 | 2.00 | 4.00 | 4.00 | 2.00 | 16.00 |
| E. coli ATCC 25922 | 1.00 | 0.50 | 1.00 | 2.00 | 4.00 | 4.00 | 2.00 | 16.00 |
| E. coli J3272 (tetD) | 32.00 | 0.25 | 1.00 | 1.00 | 1.00 | 2.00 | 1.00 | 16.00 |
| Serr. marc. FPOR 87-33 | 16.00 | 8.00 | 32.00 | >32.00 | >32.00 | >32.00 | 16.00 | >32.00 |
| X. maltophilia NEMC 87-2 | 1.00 | 4.00 | 16.00 | 32.00 | >32.00 | >32.00 | 32.00 | 32.00 |
| Ps. aeruginosa ATCC 2785 | 32.00 | 16.00 | 32.00 | >32.00 | >32.00 | >32.00 | >32.00 | >32.00 |
| S aureus NEMC 89-4 (MRSA) | 0.12 | 0.25 | 1.00 | 0.50 | 2.00 | 2.00 | 2.00 | 2.00 |
| S. aureus UBMS 88-4 (par 88-5, tetM) | 0.06 | 0.25 | 1.00 | 0.50 | 1.00 | 2.00 | 2.00 | 1.00 |
| S. aureus UBMS 88-5 (tetM) | 8.00 | 0.50 | 1.00 | 1.00 | 4.00 | 4.00 | 4.00 | 2.00 |
| S. aureus UBMS 88-7 (tetK) | 4.00 | 4.00 | 2.00 | 4.00 | 16.00 | 2.00 | 4.00 | 2.00 |
| S. aureus UBMS 90-1 (tetM) | 8.00 | 0.50 | 1.00 | 2.00 | 8.00 | 8.00 | 4.00 | 2.00 |
| S. aureus UBMS 90-3 | 0.06 | 0.12 | 0.50 | 0.50 | 1.00 | 0.50 | 1.00 | 1.00 |
| S. aureus UBMS 90-2 (tetM) | 8.00 | 0.50 | 0.50 | 0.50 | 2.00 | 2.00 | 2.00 | 2.00 |
| S. aureus IVES 2943 (tet-resist) | 16.00 | 8.00 | 4.00 | 16.00 | 32.00 | 4.00 | 32.00 | 2.00 |
| S. aureus ROSE MP (tet-resist) | 8.00 | 8.00 | 8.00 | 32.00 | >32.00 | 8.00 | >32.00 | 8.00 |
| S. aureus SMITH MP (mino-sens) | 0.12 | 0.25 | 0.50 | 0.50 | 0.50 | 1.00 | 2.00 | 4.00 |
| S. aureus IVES 1983 MP | 16.00 | 8.00 | 2.00 | 8.00 | 32.00 | 8.00 | 32.00 | 2.00 |
| S. aureus ATCC 29213 | 0.06 | 0.25 | 1.00 | 1.00 | 1.00 | 2.00 | 2.00 | 2.00 |
| S. hemolyticus AVAH 88-3 | 0.25 | 0.50 | 2.00 | 8.00 | 8.00 | 8.00 | 4.00 | 4.00 |
| Enterococcus 12201 (vanc-resist.) | 8.00 | 0.50 | 0.50 | 1.00 | 4.00 | 2.00 | 4.00 | 1.00 |
| E. faecalis ATCC 29212 | 4.00 | 0.25 | 0.25 | 0.50 | 0.50 | 0.50 | 2.00 | 1.00 |

| ORGANISM | Doxycycline | H | I | J | K | L | M | N |
|---|---|---|---|---|---|---|---|---|
| E. coli UBMS 88-1 (tetB) | 32.00 | 8.00 | 8.00 | 16.00 | >32.00 | 16.00 | >32.00 | >32.00 |
| E. coli MC4100 (tet-sensitive) | 0.25 | 1.00 | 2.00 | 2.00 | 4.00 | 4.00 | >32.00 | >32.00 |
| E. coli PRP1 (tetA) | 8.00 | 16.00 | 16.00 | 32.00 | >32.00 | >32.00 | >32.00 | >32.00 |
| E. coli MC4100 (TN10WT) | >32.00 | 4.00 | 8.00 | 16.00 | >32.00 | 32.00 | >32.00 | >32.00 |
| E. coli J3272 (tetC) | 8.00 | 8.00 | 8.00 | 16.00 | >32.00 | >32.00 | >32.00 | >32.00 |
| E. coli UBMS 89-1 (tetM) | 16.00 | 4.00 | 8.00 | 16.00 | >32.00 | 8.00 | >32.00 | >32.00 |
| E. coil UBMS 89-2 (tet-sensitive) | 2.00 | 8.00 | 8.00 | 16.00 | 16.00 | 8.00 | >32.00 | >32.00 |
| E. coli J2175 (par J2445) | 2.00 | 4.00 | 8.00 | 16.00 | 16.00 | 8.00 | >32.00 | >32.00 |
| E. coli J2445 (IMP mut) | 0.25 | 1.00 | 1.00 | 1.00 | 4.00 | 4.00 | >32.00 | >32.00 |
| E. coli UBMS 90-4 (tetM) | 32.00 | 4.00 | 4.00 | 8.00 | >32.00 | 8.00 | >32.00 | >32.00 |
| E. coli UBMS 90-5 K-12 | 1.00 | 4.00 | 8.00 | 8.00 | 16.00 | 8.00 | >32.00 | >32.00 |
| E. coli #311 MP (Mino-sensitive) | 1.00 | 4.00 | 8.00 | 16.00 | 16.00 | 8.00 | >32.00 | >32.00 |
| E. coli ATCC 25922 | 1.00 | 4.00 | 8.00 | 16.00 | 16.00 | 8.00 | >32.00 | >32.00 |
| E. coli J3272 (tetD) | 32.00 | 2.00 | 4.00 | 8.00 | >32.00 | 8.00 | >32.00 | >32.00 |
| Sar. marc. FPOR 87-33 | 16.00 | >32.00 | >32.00 | >32.00 | >32.00 | 32.00 | >32.00 | >32.00 |
| X. maltophilia NEMC 87-2 | 1.00 | >32.00 | >32.00 | >32.00 | 16.00 | >32.00 | >32.00 | >32.00 |
| Ps. aeruginosa ATCC 2785 | 32.00 | >32.00 | >32.00 | >32.00 | >32.00 | >32.00 | >32.00 | >32.00 |
| S. aureus NEMC 89-4 (MRSA) | 0.12 | 2.00 | 4.00 | 2.00 | 2.00 | 8.00 | 16.00 | >32.00 |
| S. aureus UBMS 88-4 (par 88-5, tetM) | 0.06 | 2.00 | 4.00 | 2.00 | 2.00 | 8.00 | 16.00 | >32.00 |
| S. aureus UBMS 88-5 (tetM) | 8.00 | 2.00 | 4.00 | 2.00 | >32.00 | 16.00 | >32.00 | >32.00 |
| S. aureus UBMS 88-7 (tetK) | 4.00 | 2.00 | 16.00 | 32.00 | 32.00 | >32.00 | 16.00 | 16.00 |
| S. aureus UBMS 90-1 (tetM) | 8.00 | 2.00 | 4.00 | 4.00 | >32.00 | 16.00 | >32.00 | >32.00 |
| S. aureus UBMS 90-3 | 0.06 | 1.00 | 2.00 | 0.50 | 1.00 | 4.00 | 8.00 | >32.00 |
| S. aureus UBMS 90-2 (tetM) | 8.00 | 1.00 | 4.00 | 1.00 | >32.00 | 8.00 | >32.00 | >32.00 |
| S. aureus IVES 2943 (tet-resist) | 16.00 | 2.00 | 32.00 | >32.00 | >32.00 | >32.00 | >32.00 | >32.00 |
| S. aureus ROSE MP (tet-resist) | 8.00 | 16.00 | 32.00 | >32.00 | >32.00 | >32.00 | >32.00 | >32.00 |
| S. aureus SMITH MP (mino-sens) | 0.12 | 2.00 | 1.00 | 1.00 | 4.00 | 8.00 | 8.00 | >32.00 |
| S. aureus IVES 1983 MP | 16.00 | 4.00 | 16.00 | >32.00 | >32.00 | >32.00 | >32.00 | >32.00 |
| S. aureus ATCC 29213 | 0.06 | 4.00 | 4.00 | 2.00 | 2.00 | 8.00 | 16.00 | >32.00 |
| S. hemolyticus AVAH 88-3 | 0.25 | 16.00 | 16.00 | 16.00 | 4.00 | 16.00 | >32.00 | >32.00 |
| Enterococcus 12201 (vanc-resist.) | 8.00 | 2.00 | 2.00 | 1.00 | >32.00 | 16.00 | >32.00 | >32.00 |
| E. faecalis ATCC 29212 | 4.00 | 1.00 | 1.00 | 0.50 | >32.00 | 4.00 | >32.00 | >32.00 |

When the compounds are employed an antibacterials, they can be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing for example, from about 20 to 50% ethanol and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

An effective amount of compound from 2.0 mg/kg of body weight to 100.0 mg/kg of body weight should be administered one to five times per day via any typical route of administration including but not limited to oral, parenteral (including subcutaneous, intravenous, intramuscular, intrasternal injection or infusion techniques), topical or rectal, in dosage unit formulations containing conventional non-toxic pharmaceutically acceptable carriers, adjuvants and vehicles. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserve against the contaminating action of micoorganisms such as bacterial and fungi. The carrier can be a solvent or dispersion medium containing, for example, water, ethanol, polyol (e.g., glycerol, propylene glycol and liquid polyethylene glycol), suitable mixtures thereof, and vegetable oil.

The invention will be more fully described in conjunction with the following specific examples which are not be construed as limiting the scope of the invention.

EXAMPLE 1

[4S-(4alpha,12aalpha)]-9-[(Bromoacetyl)amino]-4-(dimethylamino)-1,4,4a,5,5a,6,11,12a-octahydro-3,5,10,12,12a-pentahydroxy-6-methyl-1,11-dioxo-2-naphthacenecarboxamide A stirred mixture of 0.030 g of 9-amino-5-hydroxy-6-deoxytetracycline, 0.10 g of sodium bicarbonate and 1 ml of N-methylpyrrolidinone at ambient temperature, is treated with 0.010 ml of bromoacetyl bromide. After 20 minutes, the suspension is filtered into stirred diethyl ether and the crude product is filtered. The crude product is purified by preparative HPLC to give 0.015 g of the desired product as a yellow glass.

MS(FAB): m/z 579 (M+H) and 581 (M+H).

$^1$H NMR (CD$_3$OH): δ 8.20(d,1H,J=8.3 Hz,H-8); 6.90(d, 1H, J=8.3 Hz,H-7); 4.37(bs,1H,H-4); 4.08(s,2H,CH$_2$Br); 3.52(dd,1H,J=8.25;11.40 Hz,H-5); 2.92(bs,6H,NMe$_2$); 2.70–2.90(m,2H,H-4a and H-6); 2.51(dd,J=8.25;12.36 Hz, H-5a) and 1.50(d,3H,J=6.7 Hz,C-CH$_3$).

EXAMPLE 2

[4S-(4alpha,12aalpha)]-9-[(Bromoacetyl)amino]-4-(dimethylamino)-1,4,4a,5,5a,6,11,12a-octahydro-3,5,10,12,12a-pentahydroxy-6-methyl-1,11-dioxo-2-naphthacenecarboxamide monohydrobromide To a room temperature solution of 1.75 g of 9-amino-5-hydroxy-6-deoxytetracycline monosulfate, 20 ml of 1,3-dimethyl-3,4,5,6-tetrahydro-2(1H)-pyrimidone, hereinafter called DMPU, and 4 ml of acetonitrile is added 0.60 g of sodium carbonate. The mixture is stirred for 5 minutes followed by addition of 1.100 g of bromoacetyl bromide. The reaction is stirred one hour, filtered, and the filtrate added dropwise to a mixture of 50 ml of isopropanol and 500 ml of diethyl ether. The resulting yellow solid is collected, washed first with the mixed solvent (isopropanol and diethyl ether), followed by diethyl ether and dried to give 1.40 g of product.

MS(FAB): m/z 579 (M+H) and 581 (M+H).

EXAMPLE 3

[4S-(4alpha,12aalpha)]-9-[(Chloroacetyl)amino]-4-(dimethylamino)-1,4,4a,5,5a,6,11,12a-octahydro-3,5,10,12,12a-pentahydroxy-6-methyl-1,11-dioxo-2-naphthacenecarboxamide monohydrochloride To a room temperature solution of 0.05 g of 9-amino-5-hydroxy-6-deoxytetracycline hydrochloride, 1.5 ml of DMPU and 0.5 ml of acetonitrile is added 0.023 g of chloroacetyl chloride. The mixture is stirred for 30 minutes, then poured into a mixture of 0.5 ml of methyl alcohol, 2 ml of isopropyl alcohol and 20 ml of diethyl ether. The resulting solid is collected, washed with diethyl ether and dried to give 0.040 g of the desired product.

MS (FAB): m/z 535 (M+H) and 537 (M+H).

EXAMPLE 4

[4S-(4alpha,12aalpha)]-9-[(2-Bromo-1-oxopropyl)amino](dimethylamino)-1,4,4a,5,5a,6,11,12a-octahydro-3,5,10,12,12a-pentahydroxy-6-methyl-1,11-dioxo-2-naphthacenecarboxamide monohydrobromide The title compound is prepared by the procedure of Example 2, using 2.0 g of 9-amino-5-hydroxy-6-deoxytetracycline hydrochloride, 0.7 g of sodium carbonate, 20 ml of DMPU, 8 ml of acetonitrile and 1.73 g of 2-bromopropionyl bromide. The reaction is stirred for 1 hour to give 1.55 g of the desired product. This reaction works equally well without sodium carbonate.

MS(FAB): m/z 593 (M+H) and 595 (M+H).

EXAMPLE 5

[7S-(7alpha,10aalpha)]-N-[9-(Aminocarbonyl)-7-(dimethylamino)-5,5a,6,6a,7,10,10a,12-octahydro-1,6,8,10a,11-pentahydroxy-5-methyl-10,12-dioxo-2-naphthacenyl]-1-piperidineacetamide A solution of 0.108 g of product from Example 1, 1 ml of piperidine and 2 ml of N-methylpyrrolidone, under argon, is stirred at room temperature for 30 minutes. The reaction is concentrated in vacuo and the residue diluted with 1 ml of methanol. The solution is added dropwise to 100 ml of diethyl ether and the precipitate collected, washed with diethyl ether and dried to give a yellow product. The yellow solid is purified by preparative HPLC to give 0.045 g of the desired product as a yellow glass.

MS (FAB): m/z 585 (M+H).

$^1$H NMR (CD$_3$OH): δ 8.23(d,1H,J=8.3 Hz,H-8); 6.95(d,1H, J=8.3 Hz,H-7); 4.37(bs,1H,H-4); 4.13(s,2H,COCH$_2$N); 3.52(dd,1H,J=8.25;11.40 Hz,H-5); 2.92(bs,6H,NMe$_2$); 2.70–2.90(m,2H,H-4a and H-6); 2.51(dd,J=8.25;12.36 Hz, H-5a); 2.3–2.55(m,4H); 1.70–1.99(m,6H) and 1.51(d,3H, J=6.7 Hz, C-CH$_3$).

EXAMPLE 6

[7S-(7alpha,10aalpha)]-N-[9-(Aminocarbonyl)-7-(dimethylamino)-5,5a,6,6a,7,10,10a,12-octahydro-1,6,8,10a,11-pentahydroxy-5-methyl-10,12-dioxo-2-naphthacenyl]-1-piperidineacetamide dihydrochloride A solution of 0.215 g of product from Example 1, 4 ml of piperidine and 4 ml of N-methylpyrrolidone, under argon, is stirred at room temperature for 30 minutes. The reaction is concentrated in vacuo and the residue diluted with 2 ml of methanol and added dropwise to 150 ml of diethyl ether. 2M hydrochloric acid in diethyl ether is added to give a yellow solid. The resulting solid is collected, washed with diethyl ether and dried to give 0.20 g of product.

MS (FAB): m/z 585 (M+H).

Substantially following the methods described in detail hereinabove, in Examples 5 or 6, the compounds of this invention listed below in Examples 7–22 are prepared.

| Example # | Name | Starting Material Prod. of Exp. | Reactant | Rx Time | MS(FAB): m/z |
|---|---|---|---|---|---|
| 7 | [4S-(4alpha,12aalpha)]-4-(dimethyl-amino)-1,4,4a,5,5a,6,11,12a-octahydro-3,5,10,12,12a-pentahydroxy-6-methyl-9-[[(methylamino)acetyl]amino]-1,11-dioxo-2-naphthacenecarboxamide dihydrochloride | 1 | Methylamine (40% in water) | 2.5 hrs. | 531(M + H) |
| 8 | [4S-(4alpha,12aalpha)]-4-(Dimethyl-amino)-9-[[(ethylamino)acetyl]amino]-1,4,4a,5,5a,6,11,12a-octahydro-3,5,10,-12,12a-pentahydroxy-6-methyl-1,11-dioxo-2-naphthacenecarboxamide dihydrochloride | 1 | Ethylamine (70% in water) | 2.0 hr. | 545(M + H) |
| 9 | [7S-(7alpha,10aalpha)]-N-[9-(Amino-carbonyl)-7-(dimethylamino)-5,5a,6,6a,-7,10,10a,12-octahydro-1,6,8,10a,11-penta-hydroxy-5-methyl-10,12-dioxo-2-naphtha-cenyl]-1-pyrrolidineacetamide | 1 | Pyrrolidine | 2.0 hr. | 571(M + H) |
| 10 | [7S-(7alpha,10aalpha)]-N-[9-(Aminocar-bonyl)-7-(dimethylamino)-5,5a,6,6a,7,10,-10a,12-octahydro-1,6,8,10a,11-pentahydroxy-5-methyl-10,12-dioxo-2-naphthacenyl]-4-methyl-1-piperidineacetamide | 2 | 4-Methyl-piperidine | 1.0 hr. | 599(M + H) |
| 11 | [4S-(4alpha,12aalpha)]-4-(Dimethylamino)-1,4,4a,5,5a,6,11,12a-octahydro-3,5,10,12,12a-pentahydroxy-6-methyl-1,11-dioxo-9-[[(propylamino)acetyl]amino]-2-naphtha-cenecarboxamide dihydrochloride | 2 | Propylamine | 1 hr. | 559(M + H) |
| 12 | [4S-(4alpha,12aalpha)]-9-[[(Butyl-amino)acetyl]amino]-4-(dimethyl-amino)-1,4,4a,5,5a,6,11,12a-octa-hydro-3,5,10,12,12a-pentahydroxy-6-methyl-1,11-dioxo-2-naphthacenecar-boxamide | 2 | n-Butylamine | 2 hr. | 573 (M + H) |
| 13 | [4S-(4alpha,12aalpha)]-4-(Dimethyl-amino)-9-[[2-(dimethylamino)-1-oxo-propyl]amino]-1,4,4a,5,5a,6,11,12a-octahydro-3,5,10,12,12a-pentahydroxy-6-methyl-1,11-dioxo-2-naphthacene-carboxamide dihydrochloride | 4 | Dimethylamine | 2 hr. | 559 (M + H) |
| 14 | [4S-(4alpha,12aalpha)]-4-(Dimethyl-amino)-1,4,4a,5,5a,6,11,12a-octa-hydro-3,5,10,12,12a-pentahydroxy-6-methyl-1,11-dioxo-9-[[(pentylamino)-acetyl]amino]-2-naphthacenecarbox-amide monohydrochloride | 1 | Amylamine | 2 hr. | 587(M + H) |
| 15 | [4S-(4alpha,12aalpha)]-4-(Dimethyl-amino)-9-[[(dimethylamino)acetyl]-amino]-1,4,4a,5,5a,6,11,12a-octahydro-3,5,10,12,12a-pentahydroxy-6-methyl-1,11-dioxo-2-naphthacenecarboxamide | 1 | Dimethylamine | 2 hr. | 545 (M + H) |

-continued

| Example # | Name | Starting Material Prod. of Exp. | Reactant | Rx Time | MS(FAB): m/z |
|---|---|---|---|---|---|
| 16 | [4S-(4alpha,12aalpha)]-4-(Dimethyl-amino)-1,4,4a,5,5a,6,11,12a-octa-hydro-3,5,10,12,12a-pentahydroxy-6-methyl-1,11-dioxo-9-[[[(phenylmethyl)-amino]acetyl]amino]-2-naphthacenecar-boxamide dihydrochloride | 1 | Benzylamine | 2 hr. | 607(M + H) |
| 17 | [4S-(4alpha,12aalpha)]-4-(Dimethyl-amino)-1,4,4a,5,5a,6,11,12a-octa-hydro-3,5,10,12,12a-pentahydroxy-6-methyl-1,11-dioxo-9-[[[(2-thienyl-methyl)amino]acetyl]amino]-2-naphtha-cenecarboxamide dihydrochloride | 1 | 2-Thiophene-methylamine | 1½ hr. | 613(M + H) |
| 18 | [4S-(4alpha,12aalpha)]-4-(Dimethyl-amino)-1,4,4a,5,5a,6,11,12a-octa-hydro-3,5,10,12,12a-pentahydroxy-6-methyl-9-[[[(2-methylpropyl)amino]-acetyl]amino]-1,11-dioxo-2-naphtha-cenecarboxamide dihydrochloride | 3 | Isobutylamine | 2 hr. | 573(M + H) |
| 19 | [4S-(4alpha,12aalpha)]-4-(Dimethyl-amino)-1,4,4a,5,5a,6,11,12a-octa-hydro-3,5,10,12,12a-pentahydroxy-6-methyl-1,11-dioxo-9-[[[(2-pyridinyl-methyl)amino]acetyl]amino]-2-naphtha-cenecarboxamide dihydrochloride | 3 | 2-(Aminomethyl) pyridine | 1½ hr. | 608 (M + H) |
| 20 | [4S-(4alpha,12aalpha)]-9-[[(Diethyl-amino)acetyl]amino]-4-(dimethylamino)-1,4,4a,5,5a,6,11,12a-octahydro-3,5,10,-12,12a-pentahydroxy-6-methyl-1,11-dioxo-2-naphthacenecarboxamide | 1 | Diethylamine | 1½ hr. | 573 (M + H) |
| 21 | [7S-(7alpha,10aalpha)]-N-9-(Aminocar-bonyl)-7-(dimethylamino)-5,5a,6,6a,7,-10,10a,12-octahydro-1,6,8,10a,11-penta-hydroxy-5-methyl-10,12-dioxo-2-naphtha-cenyl]-alpha-methyl-1-pyrrolidinecar-boxamide | 3 | 2-Methyl-pyrrolidine | 1 hr. | 583 (M + H) |
| 22 | [4S-(4alpha,12aalpha)]-9-[[[(Cyclo-propylmethyl)amino]acetyl]amino]-4-(dimethylamino)-1,4,4a,5,5a,6,11,12a-octahydro-3,5,10,12,12a-pentahydroxy-6-methyl-1,11-dioxo-2-naphthacene-carboxamide dihydrochloride | 3 | (Aminomethyl) cyclopropane | 1 hr. | 571 (M + H) |
| 23 | [4S-(4alpha,12aalpha)]-4-(Dimethyl-amino)-9-[[(t-butylamino)acetyl]-amino]-1,4,4a,5,5a,6,11,12a-octa-hydro-3,5,10,12,12a-pentahydroxy-6-methyl-1,11-dioxo-2-naphthacenecar-boxamide | 1 | t-Butylamine | 2 hr. | 573 (M + H) |

EXAMPLE 24

General Procedure for the preparation of Mannich Bases

A mixture of 0.5 mm of product from Example 23 (free base), 3 ml of t-butyl alcohol, 0.55 mm of 37% formaldehyde, and 0.55 mm of pyrrolidine, morpholine or piperidine is stirred at room temperature for 30 minutes followed by heating at 100° C. for 15 minutes. The reaction mixture is cooled to room temperature and triturated with diethyl ether and hexane. The solid is collected, washed with diethyl ether and hexane, and dried to give the desired product. In this manner the following compound is made:
[4S-(4alpha,12aalpha)]-4-(Dimethylamino)-9-[[(t-butylamino)acetyl]amino]-1,4,4a,5,5a,6,11,12a-octahydro-3,5,10,12,12a-pentahydroxy-6-methyl-1,11-dioxo-N-(1-pyrrolidinylmethyl)-2-naphthacenecarboxamide Substantially following the method described in Example 5, the compounds of this invention listed below in Examples 25–48 are prepared using the product from Examples 1, 2 or 3.

EXAMPLE 25

[4S-(4alpha,12aalpha)]-4-(Dimethylamino)-1,4,4a,5,5a,6,11,12a-octahydro-3,5,10,12,12a-pentahydroxy-6-methyl-9-[[(methoxyamino)acetyl]amino]-1,11-dioxo-2-naphthacenecarboxamide

EXAMPLE 26

[4S-(4alpha,12aalpha)]-4-(Dimethylamino)-1,4,4a,5,5a,6,11,12a-octahydro-3,5,10,12,12a-pentahydroxy-6-methyl-1,11-dioxo-9-[[[(phenylmethoxy) amino]acetyl]amino]-2-naphthacenecarboxamide

EXAMPLE 27

[7S-(7alpha,10aalpha)]-N-[9-(Aminocarbonyl)-7-(dimethylamino)-5,5a,6,6a,7,10,10a,12-octahydro-1,6,8,10a,11-pentahydroxy-5-methyl-10,12-dioxo-2-naphthacenyl]-4-ethyl-1H-pyrazole-1-acetamide

EXAMPLE 28

[4S-(4alpha,12aalpha)]-9-[[(Cyclobutylmethylamino) acetyl]amino]-4-(dimethylamino)-1,4,4a,5,5a,6,11,12a-octahydro-3,5,10,12,12a-pentahydroxy-6-methyl-1,11-dioxo-2-naphthacenecarboxamide

EXAMPLE 29

[4S-(4alpha,12aalpha)]-9-[[(2-Butenylamino)acetyl]amino]-4-(dimethylamino)-1,4,4a,5,5a,6,11,12a-octahydro-3,5,10,12,12a-pentahydroxy-6-methyl-1,11-dioxonaphthacenecarboxamide

EXAMPLE 30

[4S-(4alpha,12aalpha)]-4-(Dimethylamino)-1,4,4a,5,5a,6,11,12a-octahydro-3,5,10,12,12a-pentahydroxy-6-methyl-9-[[(hydroxyamino)acetyl]amino]-1,11-dioxo-2-naphthacenecarboxamide

EXAMPLE 31

[4S-(4alpha,12aalpha)]-4-(Dimethylamino)-1,4,4a,5,5a,6,11,12a-octahydro-3,5,10,12,12a-pentahydroxy-6-methyl-1,11-dioxo-9-[[[methyl(phenylmethyl)amino]acetyl]amino]-2-naphthacenecarboxamide

EXAMPLE 32

[7S-(7alpha,10aalpha)]-N[9-(Aminocarbonyl)-7-(dimethylamino)-5,5a,6,6a,7,10,10a,12-octahydro-1,6,8,10a,11-pentahydroxy-5-methyl-10,12-dioxo-2-naphthacenyl]-5-methyl-2,5-diazabicyclo[2.2.1]heptane-2-acetamide

EXAMPLE 33

[7S-[7alpha,10aalpha)]-N-[9-(Aminocarbonyl)-7-(dimethylamino)-5,5a,6,6a,7,10,10a,12-octahydro-1,6,8,10a,11-pentahydroxy-5-methyl-10,12-dioxo-2-naphthacenyl]-3-methyl-4-morpholineacetamide

EXAMPLE 34

[7S-(7alpha,10aalpha)]-N-[9-(Aminocarbonyl)-7-(dimethylamino)-5,5a,6,6a,7,10,10a,12-octahydro-1,6,8,10a,11-pentahydroxy-5-methyl-10,12-dioxo-2-naphthacenyl]-2-azabicyclo[2.2.1]heptane-2-acetamide

EXAMPLE 35

[7S-(7alpha,10aalpha)]-N-[9-(Aminocarbonyl)-7-(dimethylamino)-5,5.a,6,6a,7,10,10a,12-octahydro-1,6,8,10a,11-pentahydroxy-5-methyl-10,12-dioxo-2-naphthacenyl]-6-methyl-2-azabicyclo[2.2.2]octane-2-acetamide

EXAMPLE 36

[7S-(7alpha,10aalpha)]-N-[9-(Aminocarbonyl)-7-(dimethylamino)-5,5a,6,6a,7,10,10a,12-octahydro-1,6,8,10a,11-pentahydroxy-5-methyl-10,12-dioxo-2-naphthacenyl]-4-methyl-1-piperazinecarboxamide

EXAMPLE 37

[7S-(7alpha,10aalpha)]-N-[9-(Aminocarbonyl)-7-(dimethylamino)-5,5a,6,6a,7,10,10a,12-octahydro-1,6,8,10a,11-pentahydroxy-5-methyl-10,12-dioxo-2-naphthacenyl]-4-hydroxy-1-piperazineacetamide

EXAMPLE 38

[7S-(7alpha,10aalpha)]-N-[9-(Aminocarbonyl)-7-(dimethylamino)-5,5a,6,6a,7,10,10a,12-octahydro-1,6,8,10a,11-pentahydroxy-5-methyl-10,12-dioxo-2-naphthacenyl]-3-methyl-1-piperazinecarboxamide

EXAMPLE 39

[7S-(7alpha,10aalpha)]-N-[9-(Aminocarbonyl)-7-(dimethylamino)-5,5a,6,6a,7,10,10a,12-octahydro-1,6,8,10a,11-pentahydroxy-5-methyl-10,12-dioxo-2-naphthacenyl]-3-cyclopropyltetrahydro-4H-thiazine-4-acetamide

EXAMPLE 40

[7S-(7alpha,10aalpha)]-N-[9-(Aminocarbonyl)-7-(dimethylamino)-5,5a,6,6a,7,10,10a,12-octahydro-1,6,8,10a,11-pentahydroxy-5-methyl-10,12-dioxo-2-naphthacenyl]-3-ethyl-1H-pyrrole-1-acetamide

EXAMPLE 41

[4S-(4alpha,12aalpha)]-4-(Dimethylamino)-1,4,4a,5,5a,6,11,12a-octahydro-3,5,10,12,12a-pentahydroxy-6-methyl-9-[[(1H-imidazol-2-ylmethylamino)acetyl]amino]-1,11-dioxo-2-naphthacenecarboxamide

EXAMPLE 42

[7S-(7alpha,10aalpha)]-N-[2-[[9-(Aminocarbonyl)-7-(dimethylamino)-5,5a,6,6a,7,10,10a,12-octahydro-1,6,8,10a,11-pentahydroxy-5-methyl-10,12-dioxo-2-naphthacenyl]amino]-2-oxoethyl]alanine

EXAMPLE 43

[7S-(7alpha,10aalpha)]-N-[2-[[9-(Aminocarbonyl)-7-(dimethylamino)-5,5a,6,6a,7,10,10a,12-octahydro-1,6,8,10a,11-pentahydroxy-5-methyl-10,12-dioxo-2-naphthacenyl]amino]-2-oxoethyl]carbamic acid 1,1-dimethyl ester

EXAMPLE 44

[4S-(4alpha,12aalpha)]-4-(Dimethylamino)-1,4,4a,5,5a,6,11,12a-octahydro-3,5,10,12,12a-pentahydroxy-6-methyl-9-[[[[(2-methylcyclopropyl)oxy]amino]acetyl]amino]-1,11-dioxo-2-naphthacenecarboxamide

EXAMPLE 45

[4S-(4alpha-12aalpha)]-9-[[[(Bicyclo[2.2.2]oct-2-yloxy)amino]acetyl]amino]-4-(dimethylamino)-1,4,4a,5,5a,6,11,12a-octahydro-3,5,10,12,12a-pentahydroxy-6-methyl-1,11-dioxo-2-naphthacenecarboxamide

EXAMPLE 46

[4S-(4alpha,12aalpha)]-4-(Dimethylamino)-1,4,4a,5,5a,6,11,12a-octahydro-3,5,10,12,12a-pentahydroxy-6-methyl-9-[[[(3-methyl-2-butenyl)amino]acetyl]amino]-1,11-dioxo-2-naphthacenecarboxamide

EXAMPLE 47

[4S-(4alpha,12aalpha)]-4-(Dimethylamino)-1,4,4a,5,5a,6,11,12a-octahydro-3,5,10,12,12a-pentahydroxy-6-methyl-9-[[[[4-[(2-methyl-1-oxopropyl)amino]phenyl]amino]acetyl]amino]-1,11-dioxo-2-naphthacenecarboxamide

EXAMPLE 48

[7S-(7alpha,10aalpha)]-N-[9-(Aminocarbonyl)-7-(dimethylamino)-5,5a,6,6a,7,10,10a,12-octahydro-1,6,8,10a,11-pentahydroxy-5-methyl-10,12-dioxo-2-naphthacenyl]-3-ethyl-1-pyrrolidineacetamide Substantially following the method described in Example 5, the compounds of this invention listed below in Examples 49–55 are prepared using the product from Example 4.

EXAMPLE 49

[4S-[4alpha,12aalpha)]-4-(Dimethylamino)-1,4,4a,5,5a,6,
11,12a-octahydro-3,5,10,12,12a-pentahydroxy-6-methyl-
9-[[2-[[(1-methyl-1H-imidazol-2-yl)methyl]amino]-1-
oxopropyl]amino]-1,11-dioxo-2-
naphthacenecarboxamide

EXAMPLE 50

[4S-(4alpha,12aalpha)]-9-[[2-(Dicyclopropylamino)-1-
oxopropyl]amino]-4-(dimethylamino)-1,4,4a,5,5a,6,11,
12a-octahydro-3,5,10,12,12a-pentahydroxy-6-methyl-1,
11-dioxo-2-naphthacenecarboxamide

EXAMPLE 51

[7S-(7alpha,10aalpha)]-N-[9-(Aminocarbonyl)-7-
(dimethylamino)-1,4,4a,5,5a,6,11,12a-octahydro-3,5,10,
12,12a-pentahydroxy-6-methyl-10,12-dioxo-2-
naphthacenyl]-4-methoxy-α-methyl-1-
piperazinecarboxamide

EXAMPLE 52

[7S-(7alpha,10aalpha)]-N-[9-(Aminocarbonyl)-7-
(dimethylamino)-5,5a,6,6a,7,10,10a,12-octahydro-1,6,8,
10a,11-pentahydroxy-5-methyl-10,12-dioxo-2-
naphthacenyl]tetrahydro-α,2-dimethyl-4H-1,4-thiazine-
4-acetamide

EXAMPLE 53

[7S-(7alpha,10aalpha)]-[2-[[9-(Aminocarbonyl)-7-
(dimethylamino]-5,5a,6,6a,7,10,10a,12-octahydro-1,6,8,
10a,11-pentahydroxy-5-methyl-10,12-dioxo-2-
naphthacenyl]amino]-2-oxo-1-methylethyl]carbamic acid
2-propenyl ester

EXAMPLE 54

[7S-(7alpha,10aalpha)]-N-[9-(Aminocarbonyl)-7-
(dimethylamino)-5,5a,6,6a,7,10,10a,12-octahydro-1,6,8,
10a,11-pentahydroxy-5-methyl-10,12-dioxo-2-
naphthacenyl]-4-(aminomethyl)-α-methyl-1-
piperidineacetamide

EXAMPLE 55

[4S-(4alpha,12aalpha)]-4-(Dimethylamino)-1,4,4a,5,5a,6,
11,12a-octahydro-3,5,10,12,12a-pentahydroxy-6-methyl-
9-[[2-[[3-(methylsulfonyl)phenyl]amino]-1-oxopropyl]
amino]-1,11-dioxo-2-naphthacenecarboxamide Substantially following the method, described in detail
herein above in Example 2, the compound of invention
Example 56 is prepared.

EXAMPLE 56

[4S-(4alpha,12aalpha)]-9-[(2-Bromo-2-methyl-1-
oxopropyl)amino]-4-(dimethylamino)-1,4,4a,5,5a,6,11,
12a-octahydro-3,5,10,12,12a-pentahydroxy-6-methyl-1,
11-dioxo-2-naphthacenecarboxamide hydrobromide

EXAMPLE 57

[4S-(4alpha,12aalpha)]-4-(Dimethylamino)-1,4,4a,5,5a,6,
11,12a-octahydro-3,5,10,12,12a-pentahydroxy-6-methyl-
9-[[2-methyl-2-(methylamino)-1-oxopropyl]amino]-1,
11-dioxo-2-naphthacenecarboxamide The titled compound is prepared by the procedure of
Example 5. The reactants are the product from Example 56
and methylamine.

EXAMPLE 58

[4S(4alpha,12aalpha)]-4-(Dimethylamino)-9-[[2-
(dimethylamino)-2-methyl-1-oxopropyl]amino]-1,4,4a,5,
5a,6,11,12a-octahydro-3,5,10,12,12a-pentahydroxy-6-
methyl-1,11-dioxo-2-naphthacenecarboxamide The titled compound is prepared by the procedure of
Example 5. The reactants are the product from Example 56
and dimethylamine.

Substantially following the method, described in detail
herein above in Example 2, the compound of invention
Example 59 is prepared.

EXAMPLE 59

[4S-(4alpha,12aalpha)]-9-[2-Bromo-1-oxobutyl)amino]-4-
(dimethylamino)-1,4,4a,5,5a,6,11,12a-octahydro-3,5,10,
12,12a-pentahydroxy-6-methyl-1,11-dioxo-2-
naphthacenecarboxamide hydrobromide

EXAMPLE 60

[4S-(4alpha,12aalpha)]-4-(Dimethylamino)-1,4,4a,5,5a,6,
11,12a-octahydro-3,5,10,12,12a-pentahydroxy-6-methyl-
9-[[(3-methylcyclobutyl)oxy]amino]-1-oxobutyl]amino]-
1,11-dioxo-2-naphthacenecarboxamide hydrobromide The titled compound is prepared by the procedure of
Example 5. The reactants are the product from Example 59
and 3-methylcyclobutyloxyamine.

EXAMPLE 61

[4S-(4alpha,12aalpha)]-9-[[2-[(1,1-dimethylethyl)
methylamino]-1-oxobutyl]amino]-4-(dimethylamino)-1,
4,4a,5,5a,6,11,12a-octahydro-3,5,10,12,12a-
pentahydroxy-6-methyl-1,11-dioxo-2-
naphthacenecarboxamide The titled compound is prepared by the procedure of
Example 5. The reactants are the product from Example 59
and N-methyl-t-butylamine.

EXAMPLE 62

[7S-(7alpha,10aalpha)]-N-[9-(Aminocarbonyl)-7-
(dimethylamino)-5,5a,6,6a,7,10,10a,12-octahydro-1,6,8,
10a,11-pentahydroxy-5-methyl-10,12-dioxo-2-
naphthacenyl]-α-ethyl-4-methyl-2-
isoxazolidineacetamide The titled compound is prepared by the procedure of
Example 5. The reactants are the product from Example 59
and 4-methyl-2-isoxazolidine,

EXAMPLE 63

[7S-(7alpha,10aalpha)]-N-[9-(Aminocarbonyl)-7-
(dimethylamino)-5,5a,6,6a,7,10,10a,12-octahydro-1,6,8,
10a,11-pentahydroxy-5-methyl-10,12-dioxo-2-
naphthacenyl]-α-ethyl-3-methyl-4H-1,2,4-triazole-4-
acetamide The titled compound is prepared by the procedure of
Example 5. The reactants are the product from Example 59
and 3-methyl-1,2,4-triazole.

Substantially following the method, described in detail
herein above in Example 2, the compound of invention
Example 64 is prepared.

EXAMPLE 64

[4S-(4alpha,12aalpha)]-9-[(2-Bromo-1-oxopentyl)amino]-
4-(dimethylamino)-1,4,4a,5,5a,6,11,12a-octahydro-3,5,
10,12,12a-pentahydroxy-6-methyl-1,11-dioxo-2-
naphthacenecarboxamide hydrobromide

EXAMPLE 65

[4S-(4alpha,12aalpha)]-4-(Dimethylamino)-9-[[2-(dimethylamino)-1-oxopentyl]amino]-1,4,4a,5,5a,6,11,12a-octahydro-3,5,10,12,12a-pentahydroxy-6-methyl-1,11-dioxo-2-naphthacenecarboxamide The titled compound is prepared by the procedure of Example 5. The reactants are the product from Example 64 and dimethylamine.

Substantially following the method, described in detail herein above in Example 2, the compound of invention Example 66 is prepared.

EXAMPLE 66

[4S,(4alpha,12aalpha)]-9-[(2-Bromo-2-methyl-1-oxobutyl)amino]-4-dimethylamino)-1,4,4a,5,5a,6,11,12a-octahydro-3,5,10,12,12a-pentahydroxy-6-methyl-1,11-dioxo-2-naphthacenecarboxamide hydrobromide

EXAMPLE 67

[4S-(4alpha,12aalpha)]-4-(Dimethylamino)-9-[[2-(ethylamino)-1-methyl-1-oxobutyl]amino]-1,4,4a,5,5a,6,11,12a-octahydro-3,5,10,12,12a-pentahydroxy-6-methyl-1,11-dioxo-2-naphthacenecarboxamide The titled compound is prepared by the procedure of Example 5. The reactants are the product from Example 66 and ethylamine.

Substantially following the method, described in detail hereinabove in Example 2, the compound of invention Example 68 is prepared.

EXAMPLE 68

[4S-(4alpha,12aalpha)]-9-[(2-Bromo-3-hydroxy-1-oxopropyl)amino]-4-(dimethylamino)-1,4,4a,5,5a,6,11,12a-octahydro-3,5,10,12,12a-pentahydroxy-6-methyl-1,11-2 -naphthacenecarboxamide hydrobromide

EXAMPLE 69

[4S-(4alpha,12aalpha)]-4-(Dimethylamino)-9-[[2-(dimethylamino)-3-hydroxy-1-oxopropyl]amino]-1,4,4a,5,5a,6,11,12a-octahydro-3,5,10,12,12a-pentahydroxy-6-methyl-1,11-dioxo-2-naphthacenecarboxamide The titled compound is prepared by the procedure of Example 5. The reactants are the product from Example 68 and dimethylamine.

EXAMPLE 70

[7S-(7alpha,10aalpha)]-N-[9-(Aminocarbonyl)-7-(dimethylamino)-5,5a,6,6a,7,10,10a,12-octahydro-1,6,8,10a,11-pentahydroxy-5-methyl-10,12-dioxo-2-naphthacenyl]-α-(hydroxymethyl)-4-methyl-1H-imidazole-1-acetamide The titled compound is prepared by the procedure of Example 5. The reactants are the product from Example 68 and 4-methylimidazole.

Substantially following the method, described in detail herein above in Example 2, the compound of invention Example 71 is prepared.

EXAMPLE 71

[4S-(4alpha,12aalpha)]-9-[[2-Bromo-3-mercapto-1-oxopropyl)amino]-4-(dimethylamino)1,4,4a,5,5a,6,11,12a-octahydro-3,5,10,12,12a-pentahydroxy-6-methyl-1,11-dioxo-2-naphthacenecarboxamide hydrobromide

EXAMPLE 72

[4S-(4alpha,12aalpha)]-9-[[2-(Diethylamino)-3-mercapto-1-oxopropyl]amino]-4-(dimethylamino)-1,4,4a,5,5a,6,11,12a-octahydro-3,5,10,12,12a-pentahydroxy-6-methyl-1,11-dioxo-2-naphthacenecarboxamide The titled compound is prepared by the procedure of Example 5. The reactants are the product from Example 71 and diethylamine.

EXAMPLE 73

[7S-(7alpha,10aalpha)]-N-[9-(Aminocarbonyl)-7-(dimethylamino)-5,5a,6,6a,7,10,10a,12-octahydro-1,6,8,10a,11-pentahydroxy-5-methyl-10-12-dioxo-2-naphthacenyl]-α-(mercaptomethyl)-1-piperazineacetamide The titled compound is prepared by the procedure of Example 5. The reactants are the product from Example 71 and piperazine.

Substantially following the method, described in detail herein above in Example 2, the compound of invention Example 74 is prepared.

EXAMPLE 74

[7S-(7alpha,10aalpha)]-4-[[9-(Aminocarbonyl)-7-(dimethylamino)-5,5a,6,6a,7,10,10a,12-octahydro-1,6,8,10a,11-pentahydroxy-5-methyl-10-12-dioxo-2-naphthacenyl]amino]-3-bromo-4-oxobutanoic acid hydrobromide

EXAMPLE 75

[7S-(7alpha,10aalpha]-4-[[9-(Aminocarbonyl)-7-(dimethylamino)-5,5a,6,6a,7,10,10a,12-octahydro-1,6,8,10a,11-pentahydroxy-5-methyl-10,11-dioxo-2-naphthacenyl]amino]-3-(hexylamino)-4-oxobutanoic acid The titled compound is prepared by the procedure by Example 5. The reactants are the product from Example 74 and n-hexylamine.

EXAMPLE 76

[7S-(7alpha,10aalpha)]-4-[[9-(Aminocarbonyl)-7-(dimethylamino)-5,5a-6,6a,7,10,10a,12-octahydro-1,6,8,10a,11-pentahydroxy-5=-methyl-10,12-dioxo-2-naphthacenyl]amino]tetrahydro-6-(hydroxymethyl]-2H-1,2-isoxazine-2-propanoic acid The titled compound is prepared by the procedure of Example 5. The reactants are the product from Example 74 and 6-(hydroxymethyl)-1,2-isoxazine.

EXAMPLE 77

[7S-(7alpha,10aalpha)]-4-[[9-(Aminocarbonyl)-7-(dimethylamino)-5,5a,6,6a,7,10,10a,12-octahydro-1,6,8,10a,11-pentahydroxy-5-methyl-10,12-dioxo-2-naphthacenyl]amino]-3-[ethyl(phenylmethyl)amino]-4-oxobutanoic acid The titled compound is prepared by the procedure of Example 5. The reactants are the product from Example 74 and N-ethylbenzylamine.

Substantially following the method, described in detail herein above in Example 2, the compound of invention Example 78 is prepared.

EXAMPLE 78

[7S-(7alpha,10aalpha)]-5-[[9-(Aminocarbonyl)-7-(dimethylamino)-5,5a,6,6a,7,10,10a,12-octahydro-1,6,8,10a-11-pentahydroxy-5-methyl-10,12-dioxo-2-naphthacenyl]amino]-4-bromo-5-oxopentanoic acid hydrobromide

EXAMPLE 79

[7S-(7alpha,10aalpha)]-5-[[9-(Aminocarbonyl)-7-(dimethylamino)-5,5a,6,6a,7,10,10a,12-octahydro-1,6,8,10a,11-pentahydroxy-5-methyl-10,12-dioxo-2-naphthacenyl]amino]-4-(cyclopropylamino)-5-oxopentanoic acid The titled compound is prepared by procedure of Example 5. The reactants are the product from Example 78 and cyclopropylamine.

Substantially following the method, described in detail herein above in Example 2, the compound of invention Example 80 is prepared.

EXAMPLE 80

[4S-(4alpha,12aalpha)]-9[(α-Bromophenylacetyl)amino]-4-(dimethylamino)-1,4,4a,5,5a,6,11,12a-octahydro-3,5,10,12,12a-pentahydroxy-6-methyl-1,11-dioxo-2-naphthacenecarboxamide hydrobromide

EXAMPLE 81

[4S-(4alpha,12aalpha)]-4-(Dimethylamino)-9-[[2-(dimethylamino)-2-phenylacetyl]amino]-1,4,4a,5,5a,6,11,12a-octahydro-3,5,10,12,12a-pentahydroxy-6-methyl-1-11-dioxo-2-naphthacenecarboxamide The titled compound is prepared by the procedure of Example 5. The reactants are the product from Example 80 and dimethylamine.

Substantially following the method, described in detail herein above in Example 2, the compound of invention Example 82 is prepared.

EXAMPLE 82

[4S-(4alpha,12aalpha)]-9-[[Bromo(4-hydroxyphenyl)acetyl]amino]-4-(dimethylamino)-1,4,4a,5,5a,6,11,12a-octahydro-3,5,10,12,12a-pentahydroxy-6-methyl-1,11-dioxo-2-naphthacenecarboxamide hydrobromide

EXAMPLE 83

[4S-(4alpha,12aalpha)]-9-[[(Butylamino)(4-hydroxyphenyl)acetyl]amino]-4-(dimethylamino)-1,4,4a,5,5a,6,11,12a-octahydro-3,5,10,12,12a-pentahydroxy-6-methyl-1,11-dioxo-2-naphthacenecarboxamide The titled compound is prepared by the procedure of Example 5. The reactants are the product from Example 82 and n-butylamine.

Substantially following the method, described in detail herein above in Example 2, the compound of invention Example 84 is prepared.

EXAMPLE 84

[4S-(4alpha,12aalpha)]-9-[[Bromo(4-methoxyphenyl)acetyl]amino]-4-(dimethylamino)-1,4,4a,5,5a,6,11,12a-octahydro-3,5,10,12,12a-pentahydroxy-6-methyl-1,11-dioxo-2-naphthacenecarboxamide hydrobromide

EXAMPLE 85

[4S-(4alpha,12aalpha)]-4-(Dimethylamino)-9-[2-(dimethylamino)-2-(4-methoxyphenyl)acetyl]-1,4,4a,5,5a,6,11,12a-octahydro-3,5,10,12,12a-pentahydroxy-6-methyl-1-11-dioxo-2-naphthacenecarboxamide The titled compound is prepared by the procedure of Example 5. The reactants are the product from Example 84 and dimethylamine.

Substantially following the method, described in detail herein above in Example 2, the compound of invention Example 86 is prepared.

EXAMPLE 86

[4S-(4alpha,12aalpha)]-9-[[Bromo[4-(trifluoromethyl)phenyl]acetyl]amino]-4-(dimethylamino)-1,4,4a,5,5a,6,11,12a-octahydro-3,5,10,12,12a-pentahydroxy-6-methyl-1,11-dioxo-2-naphthacenecarboxamide hydrobromide

EXAMPLE 87

[4S-(4alpha,12aalpha)]-4-(Dimethylamino)-9-[[2-(ethylmethylamino)-3-[4-(trifluoromethyl)phenyl]acetyl]amino]-1,4,4a,5,5a,6,11,12a-octahydro-3,5,10,12,12a-pentahydroxy-6-methyl-1,11-dioxo-2-naphthacenecarboxamide The titled compound is prepared by the procedure of Example 5. The reactants are the product from Example 86 and N-ethylmethylamine.

Substantially following the method, described in detail herein above in Example 2, the compound of invention Example 88 is prepared.

EXAMPLE 88

[4S-(4alpha,12aalpha)]-9-[[Bromo[4-(dimethylamimo)phenyl]acetyl]amino]-4-(dimethylamino)-1,4,4a,5,5a,6,11,12a-octahydro-3,5,10,12,12a-pentahydroxy-6-methyl-1,11-dioxo-2-naphthacenecarboxamide hydrobromide

EXAMPLE 89

[4S-(4alpha12aalpha)]-4-(Dimethylamino)-9-[[[4-(dimethylamino)phenyl](2-propenylamino)acetyl]amino]-1,4,4a,5,5a,6,11,12a-octahydro-3,5,10,12,12a-pentahydroxy-6-methyl-1,11-dioxo-2-naphthacenecarboxamide The titled compound is prepared by the procedure of Example 5. The reactants are the product from Example 88 and N-allylamine.

EXAMPLE 90

[7S-(7alpha,10aalpha)]-N-[2-[[9-(Aminocarbonyl)-7-(dimethylamino)-5,5a,6,6a,7,10,10a,12-octahydro-1,6,8,10a,11-pentahydroxy-5-methyl-10,12-dioxo-2-naphthacenyl]amino]-2-oxoethyl]carbamic acid 1,1-dimethylethyl ester To a room temperature solution of 0.175 g of N-(tert-butoxycarbonyl)glycine in 5 ml of methylene chloride is added 0.91 g of dicyclohexylcarbodiimide. The reaction mixture is stirred for 30 minutes, filtered and concentrated in vacuo. The residue is dissolved in 2 ml of N-methylpyrrolidone and added to a solution of 0.142 g of 9-amino-5-hydroxy-6-deoxytetracycline in 2 ml of N-methylpyrrolidinone. After 2 hours, the solvent is concentrated in vacuo and the residue is purified by reverse phase chromatography to give 0.160 g of the desired product.

MS(FAB): m/z 617 (M+H)

$^1$H NMR (CD$_3$OH): δ 8.30(d,1H,J=8.1 Hz,H-8); 6.87(d, 1H,H-7); 4.37(bs,1H,H-4), 4.18(s,2H,CH$_2$CON—); 3.53 (dd,1H,J=8.25 and 11.40 Hz,H-5); 2.93(bs,6H,N(CH$_3$)$_2$);

2.70–2.90(m, 2H,H-4a and H-6); 2.51(dd,1H,J=8.25 and 12.36 Hz,H-5a); 1.96(s,9H,t-butyl); 1.50(d,3H,C(6)-CH$_3$).

EXAMPLE 91

[4S-(4alpha,12aalpha)]-9-[(Aminoacetyl)amino]-4-(dimethylamino)-1,4,4a,5,5a,6,11,12a-octahydro-3,5,10,12,12a-pentahydroxy-6-methyl-1,11-dioxo-2-naphthacenecarboxamide The product from Example 90 is dissolved in 4 ml of trifluoroacetic acid/anisole (9:1), stirred for 45 minutes and slowly poured into 150 ml of diethyl ether. The precipitate is collected and purified by reverse phase chromatography to give 0.10 g of the desired product as a gold glass.

MS (FAB): m/z 517 (M+H).

$^1$H NMR (CD$_3$OH): δ 8.24(d,1H,J=8.2 Hz,H-8); 6.92(d, 1H,H-7); 4.35(bs,1H,H-4); 3.91(s,2H,CH$_2$CON—); 3.52 (dd,1H,J=8.24 and 11.40 Hz,H-5); 2.92(bs,6H,N(CH$_3$)$_2$); 2.70–2.90(m,2H,H-4a and H-6); 2.52(dd,1H,J=8.24 and 12.36 Hz,H-5a); 1.50(d,3H,C(6)-CH$_2$).

EXAMPLE 92

[4S-(4alpha,12aalpha)]-9-[L-(N-Methylleucyl)amino]-4-(dimethylamino)-1,4,4a,5,5a,6,11,12a-octahydro-3,5,10,12,12a-pentahydroxy-6-methyl-1,11-dioxo-2-naphthacenecarboxamide The title compound is prepared by the tandem procedure of Examples 90 and 91. N-(tert-butoxycarbonyl)-N-methyl-L-leucine is coupled with 9-amino-5-hydroxy-6-deoxytetracycline to give the protected intermediate which is then deprotected and purified to give the desired compound.

MS(FAB): m/z 587 (M+H).

$^1$H NMR (CD$_3$OH): δ 8.11(d,1H,J=8.2 Hz,H-8); 6.97(d, 1H,H-7); 4.37(bs,1H,H-4); 4.08(dd,1H,CHCONH); 3.53 (dd,1H,J=8.25 and 11.40 Hz,H-5); 2.94(bs,6H,NMe$_2$); 2.70–2.90(m,2H,H-4a and H-6); 2.71(s,3H,NCH$_3$); 2.51(dd, 1H,J=8.25 and 12.36 Hz,H-5a); 1.52(d,3H, J=7.1 Hz, C(6)-CH$_3$); 1.5–1.6(m,3H,CH—CH$_2$C); 0.90(d,6H, Me$_2$CH).

EXAMPLE 93

[4S-(4alpha,12aalpha)-9-[(L-Glutamyl)amino]-4-(dimethylamino)-1,4,4a,5,5a,6,11,12a-octahydro-3,5,10,12,12a-pentahydroxy-6-methyl-1,11-dioxo-2-naphthacenecarboxamide The title compound is prepared by the tandem procedure of Example 90 and 91. tert-Butyl N-(tert-butoxycarbonyl)-γ-L-glutamate is coupled with 9-amino-5-hydroxy-6-deoxytetracycline to give the protected intermediate which is then deprotected and purified to give the desired compound.

MS(FAB): m/z 589 (M+H).

EXAMPLE 94

[4S-(4alpha,12aalpha)-9-[(L-Aspartyl)amino]-4-(dimethylamino)-1,4,4a,5,5a,6,11,12a-octahydro-3,5,10,12,12a-pentahydroxy-6-methyl-1,11-dioxo-2-naphthacenecarboxamide The title compound is prepared by the tandem procedure of Example 90 and 91. tert-Butyl N-(tert-butoxycarbonyl)-β-L-aspartate is coupled with 9-amino-5-hydroxy-6-deoxytetracycline to give the protected intermediate which is then deprotected and purified to give the desired compound.

MS(FAB): m/z 575 (M+H).

EXAMPLE 95

[4S-(4alpha,12aalpha)]-9[(D-Phenylalanyl)amino]-4-(dimethylamino)-1,4,4a,5,5a,6,11,12a-octahydro-3,5,10,12,12a-pentahydroxy-6-methyl-1,11-dioxo-2-naphthacenecarboxamide To a room temperature solution of 0.40 g of N-(9-fluorenylmethoxycarbonyl)-D-phenylalanine in 20 ml of methylene chloride/tetrahydrofuran (1:1) is added 0.095 g of dicyclohexylcarbodiimide. The reaction mixture is stirred for 1 hour, filtered and concentrated in vacuo. The residue is added to a solution of 0.151 g 9-amino-5-hydroxy-6-deoxytetracycline in 3 ml of N-methylpyrrolidone and the mixture is stirred for 4 hours. One ml of piperidine is added and the mixture stirred for an additional 20 minutes. The reaction mixture is slowly poured into 150 ml of stirring diethyl ether and the resulting precipitate is collected. The light yellow powder is purified by preparative chromatography to give 0.049 g of the desired product as a dark yellow glass.

MS(FAB): m/z 607 (M+H).

$^1$H NMR (CD$_3$OH): δ 8.11(d,1H,J=6.9 Hz,H-8); 7.31(bs, 5H,C$_6$H$_5$); 6.92(d,1H,H-7); 4.40(t,1H,J=8.9 Hz, CHCO); 4.37(bs,1H,H-4); 3.53(dd,J=8.25 and 11.40 Hz, H-5); 3.15 (d,2H,J=8.9 Hz,CH$_2$CHO); 2.92(bs,6H,NMe$_2$); 2.70–2.90 (m,2H,H-4a and H-6); 2.51(dd,1H,J=8.25 and 12.35 Hz,H-5a); and 1.50(d,3H,J=7.1 Hz,-C(6)-CH$_3$).

EXAMPLE 96

[4S-(4alpha,12aalpha)]-9-[(L-Phenylalanyl)amino]-4-(dimethylamino)-1,4,4a,5,5a,6,11,12a-octahydro-3,5,10,12,12a-pentahydroxy-6-methyl-1,11-dioxo-2-naphthacenecarboxamide The title compound is prepared by the procedure of Example 92 using N-(9-fluorenylmethoxycarbonyl)-L-phenylalanine as the α-aminoacyl component.

MS(FAB): m/z 607 (M+H).

$^1$H NMR (CD$_3$OH): δ 8.11(d,1H,J=6.9 Hz,H-8); 7.31(bs, 5H, C$_6$H$_5$); 6.92(d,1H,H-7); 4.40(t,1H,J=8.9 Hz; CHCO); 4.37(bs,1H,H-4); 3.53(dd,J=8.25 and 11.40 Hz, H-5); 3.15 (d,2H,J=8.9 Hz, CH$_2$CHO); 2.92(bs,6H,NMe$_2$), 2.70–2.90 (m,2H,H-4a and H-6); 2.51(dd,1H,J=8.25 and 12.35 Hz,H-5a); and 1.50(d,3H,J=7.1 Hz, C(6)-CH$_3$).

EXAMPLE 97

[4S-(4alpha,12aalpha)]-9-[[L-β-(Cyclohexyl)alanyl]amino]-4-(dimethylamino)-1,4,4a,5,5a,6,11,12a-octahydro-3,5,10,12,12a-pentahydroxy-6-methyl-1,11-dioxo-2-naphthacenecarboxamide The tile compound is prepared by the procedure of Example 92 using N-(9-fluorenylmethoxycarbonyl)-β-cyclohexyl-L-alanine as the α-aminoacyl component.

MS(FAB): m/z 613 (M+H).

EXAMPLE 98

[4S-(4alpha,12aalpha)]-9-[(L-Leucyl)amino]-4-(dimethylamino)-1,4,4a,5,5a,6,11,12a-octahydro-3,5,10,12,12a-pentahydroxy-6-methyl-1,11-dioxo-2-naphthacenecarboxamide The tile compound is prepared by the procedure of Example 92 using N-(9-fluorenylmethoxycarbonyl)-L-leucine as the α-aminoacyl component.

MS (FAB): m/z 573 (M+H).

EXAMPLE 99

[4S-(4alpha,12aalpha)-9-[(L-Glutaminyl)amino]-4-(dimethylamino)-1,4,4a,5,5a,6,11,12a-octahydro-3,5,10,12,12a-pentahydroxy-6-methyl-1,11-dioxo-2-naphthacenecarboxamide The tile compound is prepared by the procedure of Example 92 using N-(9-fluorenylmethoxycarbonyl)-L-glutamine as the α-aminoacyl component.

EXAMPLE 100

[4S-(4alpha,12aalpha)-9-[(L-Prolyl)amino]-4-(dimethylamino)-1,4,4a,5,5a,6,11,12a-octahydro-3,5,10,12,12a-pentahydroxy-6-methyl-1,11-dioxo-2-naphthacenecarboxamide The title compound is prepared by the procedure of Example 90 coupling L-proline with 9-amino-5-hydroxy-6-deoxytetracycline.

MS (FAB): m/z 557 (M+H).

EXAMPLE 101

[4S-(4alpha,12aalpha)-9-[(L-(N,N-Dimethylphenylalanyl)amino]-4-(dimethylamino)-1,4,4a,5,5a,6,11,12a-octahydro-3,5,10,12,12a-pentahydroxy-6-methyl-1,11-dioxo-2-naphthacenecarboxamide The title compound is prepared by the procedure of Example 90 coupling L-(N,N-dimethyl)phenylalanine with 9-amino-5-hydroxy-6-deoxytetracycline.

MS(FAB): m/z 635 (M+H).

EXAMPLE 102

[4S-(4alpha,12aalpha)-9-[(n-Tyrosinyl)amino]-4-(dimethylamino)-1,4,4a,5,5a,6,11,12a-octahydro-3,5,10,12,12a-pentahydroxy-6-methyl-1,11-dioxo-2-naphthacenecarboxamide To a room temperature solution of 4.60 g of N-(9-fluorenylmethoxycarbonyl)-O-(tert-butyl)-L-tyrosine in 50 ml of methylene chloride/tetrahydrofuran (1:1) is added 1.04 g of dicyclohexylcarbodiimide. The reaction mixture is stirred for 1 hour, filtered and concentrated in vacuo. The residue is added to a solution of 2.30 g 9-amino-5-hydroxy-6-deoxytetracycline in 30 ml of N-methylpyrrolidone and the mixture is stirred for 4 hours. Five ml of piperidine is added, the mixture stirred for an additional 30 minutes and concentrated in vacuo. The residue is dissolved in 30 ml of trifluoroacetic acid/anisole (9:1), stirred for 45 minutes and slowly poured into 1000 ml of diethyl ether. The resulting precipitate is collected and purified by reverse phase chromatography to give 1.3 g of the desired product as a gold glass.

MS(FAB): m/z 623 (M+H).

EXAMPLE 103

[4S-(4alpha,12aalpha)-9-[(L-Lysyl)amino]-4-(dimethylamino)-1,4,4a,5,5a,6,11,12a-octahydro-3,5,10,12,12a-pentahydroxy-6-methyl-1,11-dioxo-2-naphthacenecarboxamide The title compound is prepared by procedure of Example 102 using $N^\alpha$-(9-fluorenylmethoxycarbonyl)-$N^\gamma$-(tert-butoxycarbonyl)-L-lysine and 9-amino-5-hydroxy-6-deoxytetracycline.

MS(FAB): m/z 588 (M+H).

EXAMPLE 104

[4S-(4alpha,12aalpha)-9-[(L-Tryptophanyl)amino]-4-(dimethylamino)-1,4,4a,5,5a,6,11,12a-octahydro-3,5,10,12,12a-pentahydroxy-6-methyl-1,11-dioxo-2-naphthacenecarboxamide The titled compound is prepared by procedure of Example 102 using $N^\alpha$-(9-fluorenylmethoxycarbonyl)-N-trityl-L-tryptophan and 9-amino-5-hydroxy-6-deoxytetracycline.

MS(FAB): m/z 646 (M+H).

We claim:

1. A compound of the formula:

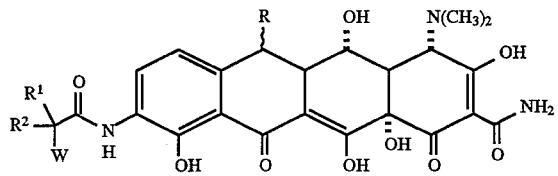

wherein:

R is selected from methylene, $\alpha$-$CH_3$ and $\beta$-$CH_3$; $R^1$ is selected from hydrogen; straight or branched ($C_1$-$C_8$) alkyl group selected from methyl, ethyl, propyl, isopropyl, butyl, isobutyl, pentyl, hexyl, heptyl and octyl; straight or branched ($C_1$-$C_8$)alkyl group optionally substituted with $\alpha$-mercapto, $\alpha$-(methylthio), $\alpha$-hydroxy, amino, guanidino or amidino; ($C_6$-$C_{10}$) aryl group selected from phenyl, $\alpha$-naphthyl and $\beta$-naphthyl; substituted ($C_6$-$C_{10}$) aryl group with substituents selected from hydroxy, halogen, ($C_1$-$C_4$) alkoxy, trihalo($C_1$-$C_3$) alkyl, nitro, amino, ($C_1$-$C_3$) alkylamino; ($C_7$-$C_9$) aralkyl group selected from benzyl, 1-phenylethyl, 2-phenylethyl and phenylpropyl; substituted ($C_7$-$C_9$) aralkyl group with substituents selected from halo, ($C_1$-$C_4$)alkyl, nitro, hydroxy, amino, mono- or di-substituted ($C_1$-$C_4$) alkylamino, ($C_1$-$C_4$)alkoxy, and ($C_1$-$C_4$)alkylsulfonyl; ($C_3$-$C_6$)cycloalkylmethyl group selected from (cyclopropyl)methyl, (cyclobutyl) methyl (cyclopentyl) methyl and (cyclohexyl)methyl;

$R^2$ is selected from hydrogen and ($C_1$-$C_6$)alkyl selected from methyl, ethyl, propyl, isopropyl, butyl, isobutyl, pentyl and hexyl;

W is selected from amino; hydroxylamino; ($C_1$-$C_{12}$) straight or branched alkyl monosubstituted amino group with substituents selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-dimethylbutyl, n-hexyl, 1-methylpentyl, 1,1-dimethylbutyl, 2,2-dimethylbutyl, 3-methylpentyl, 1,2-dimethylbutyl, 1,3-dimethylbutyl, 1-methyl-1-ethylpropyl, heptyl, octyl, nonyl, decyl, undecyl and dodecyl and the diastereomers and enantiomers of said branched alkyl monosubstituted amino group; ($C_3$-$C_8$) cycloalkyl monosubstituted amino group with substituents selected from cyclopropyl, trans-1,2-dimethylcyclopropyl, cis-1,2-dimethylcyclopropyl, cyclobutyl, cyclopentyl, cyclohexyl, cycloheptyl, cyclooctyl, bicyclo[2.2.1]hept-2-yl, and bicyclo[2.2.2] oct-2-yl and the diastereomers and enantiomers of said ($C_3$-$C_8$)cycloalkyl monosubstituted amino group; ($C_4$-$C_{10}$)cycloalkyl ($C_1$-$C_3$) alkyl monosubstituted amino group with substituents selected from (cyclopropyl)methyl, (cyclopropyl) ethyl, (cyclobutyl) methyl, (trans-2-methylcyclopropyl)methyl, and (cis-2-methylcyclobutyl)methyl; ($C_3$-$C_{10}$)alkenyl monosubstituted amino group with substituents selected from allyl, 3-butenyl, 2-butenyl (cis or trans), 2-pentenyl, 4-octenyl, 2,3-dimethyl-2-butenyl, 3-methyl-2-butenyl, 2-cyclopentenyl and 2-cyclohexenyl; ($C_6$-$C_{10}$) aryl monosubstituted amino group with substituents selected from phenyl and naphthyl; ($C_7$-$C_{10}$) aralkylamino group selected from benzylamino, 2-phenylethylamino, 1-phenylethylamino, 2-(naphthyl)methylamino, 1-(naphthyl)methylamino and phenylpropylamino; substituted phenyl amino group with substituents selected from ($C_1$-$C_5$) acyl, ($C_1$-$C_5$)acylamino, ($C_1$-$C_4$)alkyl, mono or disubstituted ($C_1$-$C_8$) alkylamino, ($C_1$-$C_4$)

alkoxy, $(C_1-C_4)$alkylsulfonyl, amino, halogen, hydroxy, nitro and trihalo $(C_1-C_3)$ alkyl; straight or branched symmetrical disubstituted $(C_2-C_8)$ alkylamino group with substituents selected from dimethyl, diethyl, diisopropyl, di-n-propyl, di-n-butyl and diisobutyl; symmetrical disubstituted $(C_3-C_{14})$ cycloalkylamino group with substituents selected from dicyclopropyl, dicyclobutyl, dicyclopentyl, dicyclohexyl and dicycloheptyl; straight or branched unsymmetrical disubstituted $(C_3-C_{14})$ alkylamino group wherein the total number of carbons in the substitution is not more than 14; unsymmetrical disubstituted $(C_4-C_{14})$ cycloalkylamino group wherein the total number of carbons in the substitution is not more than 14; $(C_1-C_4)$ alkoxyamino group selected from methoxyamino, ethoxyamino, n-propoxyamino, 1-methylethoxyamino, n-butoxyamino, 2-methylpropoxyamino, and 1,1-dimethylethoxyamino; $(C_3-C_8)$ cycloalkoxyamino group selected from cyclopropoxy, trans-1,2-dimethylcyclopropoxy, cis-1,2-dimethylcyclopropoxy, cyclobutoxy, cyclopentoxy, cyclohexoxy, cycloheptoxy, cyclooctoxy, bicyclo[2.2.1]hept-2-yloxy, and bicyclo[2.2.2]oct-2-yloxy and the diastereomers and enantiomers of said $(C_3-C_8)$ cycloalkoxyamino group; $(C_6-C_{10})$ aryloxyamino group selected from phenoxyamino, 1-naphthyloxyamino and 2-naphthyloxyamino; $(C_7-C_{11})$ arylalkoxyamino group selected from benzyloxyamino, 2-phenylethoxyamino, 1-phenylethoxyamino, 2-(naphthyl)methoxyamino, 1-(naphthyl)-methoxyamino and phenylpropoxyamino; or $R^1$ and W taken together are —$CH_2(CH_2)_nCH_2NH$—, wherein n=1–3; and the pharmacologically acceptable organic and inorganic salts or metal complexes.

2. The compound according to claim 1 wherein said inorganic salts comprise: hydrochloric, hydrobromic, hydroiodic, phosphoric, nitric or sulfate.

3. The compound according to claim 1 wherein said organic salts comprise: acetate, benzoate, citrate, cysteine or other amino acid, fumarate, glycolate, maleate, succinate, tartrate, alkylsulfonate or arylsulfonate.

4. The compound according to claim 1 wherein said metal complexes comprise: aluminum, calcium, iron, magnesium, manganese and complex salts.

5. The compound according to claim 1 wherein said inorganic salts comprise: hydrochloric, hydrobromic, hydroiodic, phosphoric, nitric or sulfate.

6. The compound according to claim 1 wherein said organic salts comprise: acetate, benzoate, citrate, cysteine or other amino acid, fumarate, glycolate, maleate, succinate, tartrate, alkylsulfonate or arylsulfonate.

7. The compound according to claim 1 wherein said metal complexes comprise: aluminum, calcium, iron, magnesium, manganese and complex salts.

8. A compound according to claim 1, [4S-(4alpha,12aalpha)]-4-(dimethylamino)-1,4,4a,5,5a,6,11,12a-octahydro-3,5,10,12,12a-pentahydroxy-6-methyl-9-[[(dimethylamino)acetyl]amino]-1,11-dioxo-2-naphthacenecarboxamide.

9. A compound according to claim 1, [4S-(4alpha,12aalpha)]-4-(dimethylamino)-9-[[(dimethylamino)acetyl]amino]-1,4,4a,5,5a,6,11,12a-octahydro-3,5,10,12,12a-pentahydroxy-6-methyl-1,11-dioxo-2-naphthacenecarboxamide monohydrochloride.

10. A compound according to claim 1, [4S-(4alpha,12aalpha)]-4-(dimethylamino)-1,4,4a,5,5a,6,11,12a-octahydro-3,5,10,12,12a-pentahydroxy-6-methyl-1,11-dioxo-9-[[(dimethylamino)acetyl]amino]-2-naphthacenecarboxamide dihydrochloride.

11. A compound according to claim 1, [4S-(4alpha,12aalpha)]-9-[[(butylamino)acetyl]amino]-4-(dimethylamino)-1,4,4a,5,5a,6,11,12a-octahydro-3,5,10,12,12a-pentahydroxy-6-methyl-1,11-dioxo-2-naphthacenecarboxamide.

12. A compound according to claim 1, [4S-(4alpha,12aalpha)]-4-(dimethylamino)-9-[[(diethylamino)acetyl]amino]-1,4,4a,5,5a,6,11,12a-octahydro-3,5,10,12,12a-pentahydroxy-6-methyl-1,11-dioxo-2-naphthacenecarboxamide.

13. A compound according to claim 1, [4S-(4alpha,12aalpha)]-4-(dimethylamino)-1,4,4a,5,5a,6,11,12a-octahydro-3,5,10,12,12a-pentahydroxy-6-methyl-1,11-dioxo-9-[[(1,1-dimethylethylamino)acetyl]amino]-2-naphthacenecarboxamide.

14. A compound according to claim 1, [4S-(4alpha,12aalpha)]-4-(dimethylamino)-1,4,4a,5,5a,6,11,12a-octahydro-3,5,10,12,12a-pentahydroxy-6-methyl-1,11-dioxo-9-[[[(phenylmethyl)amino]acetyl]amino]-2-naphthacenecarboxamide dihydrochloride.

15. A compound according to claim 1, [4S-(4alpha,12aalpha)]-4-(dimethylamino)-1,4,4a,5,5a,6,11,12a-octahydro-3,5,10,12,12a-pentahydroxy-6-methyl-9-[[[(2-methylpropyl)amino]acetyl]amino]-1,11-dioxo-2-naphthacenecarboxamide dihydrochloride.

16. A compound according to claim 1, [4S-(4alpha,12aalpha)]-4-(dimethylamino)-9-[[(methylamino)acetyl]amino]-1,4,4a,5,5a,6,11,12a-octahydro-3,5,10,12,12a-pentahydroxy-6-methyl-1,11-dioxo-2-naphthacenecarboxamide dihydrochloride.

17. A compound according to claim 1, [4S-(4alpha,12aalpha)]-9-[[[(cyclopropylmethyl)amino]acetyl]amino]-4-(dimethylamino)-1,4,4a,5,5a,6,11,12a-octahydro-3,5,10,12,12a-pentahydroxy-6-methyl-1,11-dioxo-2-naphthacenecarboxamide.

18. A compound according to claim 1, [4S-(4alpha,12aalpha)]-4-(dimethylamino)-9-[[(dimethylamino)acetyl]amino]-1,4,4a,5,5a,6,11,12a-octahydro-3,5,10,12,12a-pentahydroxy-6-methyl-1,11-dioxo-2-naphthacenecarboxamide sulfate.

19. A compound according to claim 1, [4S-(4alpha,12aalpha)]-4-(dimethylamino)-9-[[(dimethylamino)-1-oxopropyl]amino]-1,4,4a,5,5a,6,11,12a-octahydro-3,5,10,12,12a-pentahydroxy-6-methyl-1,11-dioxo-2-naphthacenecarboxamide dihydrochloride.

20. A compound according to claim 1, [4S-(4alpha,12aalpha)]-4-(dimethylamino)-9-[[(dimethylamino)-1-oxopropyl]amino]-1,4,4a,5,5a,6,11,12a-octahydro-3,5,10,12,12a-pentahydroxy-6-methyl-1,11-dioxo-2-naphthacenecarboxamide monohydrochloride.

21. A compound according to claim 1, [4S-(4alpha,12aalpha)]-4-(dimethylamino)-9-[[(dimethylamino)-1-oxopropyl]amino]-1,4,4a,5,5a,6,11,12a-octahydro-3,5,10,12,12a-pentahydroxy-6-methyl-1,11-dioxo-2-naphthacenecarboxamide.

22. A compound according to claim 1, [4S-(4alpha,12aalpha)]-4-(dimethylamino)-9-[[(hexylamino)acetyl]amino]-1,4,4a,5,5a,6,11,12a-octahydro-3,5,10,12,12a-pentahydroxy-6-methyl-1,11-dioxo-2-naphthacenecarboxamide dihydrochloride.

23. A compound according to claim 1, [4S-(4alpha,12aalpha)]-4-(Dimethylamino)-1,4,4a,5,5a,6,11,12a-octahydro-3,5,10,12,12a-pentahydroxy-6-methyl-9-[[(methoxyamino)acetyl]amino]-1,11-dioxo-2-naphthacenecarboxamide.

24. A compound according to claim 1, [4S-(4alpha,12aalpha)]-4-(Dimethylamino)-1,4,4a,5,5a,6,11,12a- octahydro-3,5,10,12,12a-pentahydroxy-6-methyl-1,11-dioxo-9-[[[(phenylmethoxy)amino]acetyl]amino]-2-naphthacenecarboxamide.

25. A compound according to claim 1, [4S-(4alpha, 12aalpha)]-9-[[(Cyclobutylmethylamino)acetyl]amino]-4-(dimethylamino)-1,4,4a,5,5a,6,11,12a-octahydro-3,5,10,12,12a-pentahydroxy-6-methyl-1,11-dioxo-2-naphthacenecarboxamide.

26. A compound according to claim 1, [4S-(4alpha, 12aalpha)]-9-[[(2-butenylamino)acetyl]amino]-4-(dimethylamino)-1,4,4a,5,5a,6,11,12a-octahydro-3,5,10,12,12a-pentahydroxy-6-methyl-1,11-dioxo-2-naphthacenecarboxamide.

27. A compound according to claim 1, [4S-(4alpha, 12aalpha)]-4-(Dimethylamino)-1,4,4a,5,5a,6,11,12a-octahydro-3,5,10,12,12a-pentahydroxy-6-methyl-9-[[(hydroxyamino)acetyl]amino]-1,11-dioxo-2-naphthacenecarboxamide.

28. A compound according to claim 1, [4S-(4alpha, 12aalpha)]-4-(Dimethylamino)-1,4,4a,5,5a,6,11,12a-octahydro-3,5,10,12,12a-pentahydroxy-6-methyl-1,11-dioxo-9-[[[methyl(phenylmethyl)amino]acetyl]amino]-2-naphthacenecarboxamide.

29. A compound according to claim 1, [4S-(4alpha, 12aalpha)]-4-(Dimethylamino)-1,4,4a,5,5a,6,11,12a-octahydro-3,5,10,12,12a-pentahydroxy-6-methyl-9-[[[[(2-methylcyclopropyl)oxy]amino]acetyl]amino]-1,11-dioxo-2-naphthacenecarboxamide.

30. A compound according to claim 1, [4S-(4alpha, 12aalpha)]-4-(Dimethylamino)-1,4,4a,5,5a,6,11,12a-octahydro-3,5,10,12,12a-pentahydroxy-6-methyl-9-[[[(3-methyl-2-butenyl)amino]acetyl]amino]-1,11-dioxo-2-naphthacenecarboxamide.

31. A compound according to claim 1, [4S-(4alpha, 12aalpha)]-4-(Dimethylamino)-1,4,4a,5,5a,6,11,12a-octahydro-3,5,10,12,12a-pentahydroxy-6-methyl-9-[[[4-[(2-methyl-1-oxopropyl)amino]phenyl]amino]acetyl]amino]-1,11-dioxo-2-naphthacenecarboxamide.

32. A compound according to claim 1, [4S-(4alpha, 12aalpha)]-9-[[2-(Dicyclopropylamino)-1-oxopropyl]amino]-4-(dimethylamino)-1,4,4a,5,5a,6,11,12a-octahydro-3,5,10,12,12a-pentahydroxy-6-methyl-1,11-dioxo-2-naphthacenecarboxamide.

33. A compound according to claim 1, [4S-(4alpha, 12aalpha)]-4-(Dimethylamino)-1,4,4a,5,5a,6,11,12a-octahydro-3,5,10,12,12a-pentahydroxy-6-methyl-9-[[2-[[3-(methylsulfonyl)phenyl]amino]-1-oxopropyl]amino]-1,11-dioxo-2-naphthacenecarboxamide.

34. A compound according to claim 1, [4S-(4alpha, 12aalpha)]-4-(Dimethylamino)-1,4,4a,5,5a,6,11,12a-octahydro-3,5,10,12,12a-pentahydroxy-6-methyl-9-[[2-methyl-2-(methylamino)-1-oxopropyl]amino]-1,11-dioxo-2-naphthacenecarboxamide.

35. A compound according to claim 1, [4S-(4alpha, 12aalpha)]-4-(Dimethylamino)-9-[[2-(dimethylamino)-2-methyl-1-oxopropyl]amino]-1,4,4a,5,5a,6,11,12a-octahydro-3,5,10,12,12a-pentahydroxy-6-methyl-1,11-dioxo-2-naphthacenecarboxamide.

36. A compound according to claim 1, [4S-(4alpha, 12aalpha)]-4-(Dimethylamino)-1,4,4a,5,5a,6,11,12a-octahydro-3,5,10,12,12a-pentahydroxy-6-methyl-9-[[2-[[(3-methylcyclobutyl)oxy]amino]-1-oxobutyl]amino]-1,11-dioxo-2-naphthacenecarboxamide hydrobromide.

37. A compound according to claim 1, [4S-(4alpha, 12aalpha)]-9-[[2-[(1,1-dimethylethyl)methylamino]-1-oxobutyl]amino]-4-(dimethylamino)-1,4,4a,5,5a,6,11,12a-octahydro-3,5,10,12,12a-pentahydroxy-6-methyl-1,11-dioxo-2-naphthacenecarboxamide.

38. A compound according to claim 1, [4S-(4alpha, 12aalpha)]-4-(Dimethylamino)-9-[[2-(dimethylamino)-3,3-dimethyl-1-oxobutyl]amino]-1,4,4a,5,5a,6,11,12a-octahydro-3,5,10,12,12a-pentahydroxy-6-methyl-1,11-dioxo-2-naphthacenecarboxamide.

39. A compound according to claim 1, [4S-(4alpha, 12aalpha)]-4-(Dimethylamino)-9-[[2-(ethylamino)-2-methyl-1-oxobutyl]amino]-1,4,4a,5,5a,6,11,12a-octahydro-3,5,10,12,12a-pentahydroxy-6-methyl-1,11-dioxo-2-naphthacenecarboxamide.

40. A compound according to claim 1, [4S-(4alpha, 12aalpha)]-4-(Dimethylamino)-9-[[2-(dimethylamino)-3-hydroxy-1-oxopropyl]amino]-1,4,4a,5,5a,6,11,12a-octahydro-3,5,10,12,12a-pentahydroxy-6-methyl-1,11-dioxo-2-naphthacenecarboxamide.

41. A compound according to claim 1, [4S-(4alpha, 12aalpha)]-9-[[2-(Diethylamino)-3-mercapto-1-oxopropyl]amino]-4-(dimethylamino)-1,4,4a,5,5a,6,11,12a-octahydro-3,5,10,12,12a-pentahydroxy-6-methyl-1,11-dioxo-2-naphthacenecarboxamide.

42. A compound according to claim 1, [4S-(4alpha, 12aalpha)]-4-(Dimethylamino)-9-[[2-(dimethylamino)-2-phenylacetyl]amino]-1,4,4a,5,Sa,6,11,12a-octahydro-3,5,10,12,12a-pentahydroxy-6-methyl-1-11-dioxo-2-naphthacenecarboxamide.

43. A compound according to claim 1, [4S-(4alpha, 12aalpha)]-9-[[(Butylamino)(4-hydroxyphenyl)acetyl]amino]-4-(dimethylamino)-1,4,4a,5,5a,6,11,12a-octahydro-3,5,10,12,12a-pentahydroxy-6-methyl-1,11-dioxo-2-naphthacenecarboxamide.

44. A compound according to claim 1, [4S-(4alpha, 12aalpha)]-4-(Dimethylamino)-9-[2-(dimethylamino)-2-(4-methoxyphenyl)acetyl]-1,4,4a,5,5a,6,11,12a-octahydro-3,5,10,12,12a-pentahydroxy-6-methyl-1-11-dioxo-2-naphthacenecarboxamide.

45. A compound according to claim 1, [4S-(4alpha, 12aalpha)]-4-(Dimethylamino)-9-[[2-(ethylmethylamino)-3-[4-(trifluoromethyl)phenyl]acetyl]amino]-1,4,4a,5,5a,6,11,12a-octahydro-3,5,10,12,12a-pentahydroxy-6-methyl-1,11-dioxo-2-naphthacenecarboxamide.

46. A compound according to claim 1, [4S-(4alpha, 12aalpha)]-4-(Dimethylamino)-9-[[[4-(dimethylamino)phenyl](2-propenylamino)acetyl]amino]-1,4,4a,5,5a,6,11,12a-octahydro-3,5,10,12,12a-pentahydroxy-6-methyl-1,11-dioxo-2-naphthacenecarboxamide.

47. A compound according to claim 1, [4S-(4alpha, 12aalpha)]-9-[(Aminoacetyl)amino]-4-(dimethylamino)-1,4,4a,5,5a,6,11,12a-octahydro-3,5,10,12,12a-pentahydroxy-6-methyl-1,11-dioxo-2-naphthacenecarboxamide.

48. A compound according to claim 1 wherein:
R is selected from methylene, α-CH$_3$ and β-CH$_3$; R$^1$ is selected from hydrogen; straight or branched (C$_1$–C$_8$) alkyl group selected from methyl, ethyl, propyl, isopropyl, butyl, isobutyl, pentyl, hexyl, heptyl and octyl; straight or branched (C$_1$–C$_8$) alkyl group optionally substituted with α-mercapto, α-(methylthio), α-hydroxy, amino, guanidino or amidino; (C$_6$–C$_{10}$) aryl group selected from phenyl, α-naphthyl and β-naphthyl; (C$_7$–C$_9$) aralkyl group selected from benzyl, 1-phenylethyl, 2-phenylethyl and phenylpropyl; substituted (C$_7$–C$_9$) aralkyl group with substituents selected from halo, (C$_1$–C$_4$)alkyl, nitro, hydroxy, amino, mono- or di-substituted (C$_1$–C$_4$)alkylamino, (C$_1$–C$_4$) alkoxy, and (C$_1$–C$_4$)alkylsulfonyl; (C$_3$–C$_6$)cycloalkylmethyl group selected from (cyclopropyl)methyl, (cyclobutyl)methyl, (cyclopentyl)methyl and (cyclohexyl)methyl; R$^2$ is selected from hydrogen and (C$_1$–C$_6$)alkyl selected from methyl, ethyl, propyl, isopropyl, butyl, isobutyl, pentyl and hexyl;

W is selected from amino; hydroxylamino; $(C_1-C_{12})$ straight or branched alkyl monosubstituted amino group with substituents selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl, 1-methyl-1-ethylpropyl, heptyl, octyl, nonyl, decyl, undecyl and dodecyl and the diastereomers and enantiomers of said branched alkyl monosubstituted amino group; $(C_3-C_8)$ cycloalkyl monosubstituted amino group with substituents selected from cyclopropyl, trans-1,2-dimethylcyclopropyl, cis-1,2-dimethylcyclopropyl, cyclobutyl, cyclopentyl, cyclohexyl, cycloheptyl, cyclooctyl, bicyclo[2.2.1]hept-2-yl, and bicyclo[2.2.2]oct-2-yl and the diastereomers and enantiomers of said $(C_3-C_8)$cycloalkyl monosubstituted amino group; $(C_4-C_{10})$cycloalkyl $(C_1-C_3)$alkyl monosubstituted amino group with substituents selected from (cyclopropyl)methyl, (cyclopropyl)ethyl, (cyclobutyl)methyl, (trans-2-methylcyclopropyl)methyl, and (cis-2-methylcyclobutyl)methyl; $(C_3-C_{10})$alkenyl monosubstituted amino group with substituents selected from allyl, 3-butenyl, 2-butenyl (cis or trans), 2-pentenyl, 4-octenyl, 2,3-dimethyl-2-butenyl, 3-methyl-2-butenyl 2-cyclopentenyl and 2-cyclohexenyl; $(C_6-C_{10})$ aryl monosubstituted amino group with substituents selected from phenyl and naphthyl; $(C_7-C_{11})$aralkylamino group selected from benzylamino, 2-phenylethylamino, 1-phenylethylamino, 2-(naphthyl)methylamino,1-(naphthyl)methylamino and phenylpropylamino; straight or branched symmetrical disubstituted $(C_2-C_8)$ alkylamino group with substituents selected from dimethyl, diethyl, diisopropyl and di-n-propyl; symmetrical disubstituted $(C_3-C_{14})$ cycloalkylamino group with substituents selected from dicyclopropyl, dicyclobutyl, dicyclopentyl, dicyclohexyl and dicycloheptyl; straight or branched unsymmetrical disubstituted $(C_3-C_{14})$alkylamino group wherein the total number of carbons in the substitution is not more than 14; unsymmetrical disubstituted $(C_4-C_{14})$ cycloalkylamino group wherein the total number of carbons in the substitution is not more than 14; $(C_1-C_4)$alkoxyamino group selected from methoxyamino, ethoxyamino, n-propoxyamino, 1-methylethoxyamino, n-butoxyamino, 2-methylpropoxyamino, and 1,1-dimethylethoxyamino; $(C_3-C_8)$cycloalkoxyamino group selected from cyclopropoxyamino, trans-1,2-dimethylcyclopropoxyamino, cis-1,2-dimethylcyclopropoxyamino, cyclobutoxy, cyclopentoxyamino, cyclohexoxyamino, cycloheptoxyamino, cyclooctoxyamino, bicyclo [2.2.1]hept-2-yloxyamino, and bicyclo[2.2.2]oct-2-yloxyamino and the diastereomers and enantiomers of said $(C_3-C_8)$ cycloalkoxyamino group; $(C_6-C_{10})$aryloxyamino group selected from phenoxyamino, 1-naphthyloxyamino and 2-naphthyloxyamino; $(C_7-C_{11})$ arylalkoxyamino group selected from benzyloxyamino, 2-phenylethoxyamino, 1-phenylethoxyamino, 2-(naphthyl)methoxyamino, 1-(naphthyl)-methoxyamino and phenylpropoxyamino; or $R^1$ and W taken together are —$CH_2(CH_2)_nCH_2NH$—, wherein n=1–3; and the pharmacologically acceptable organic and inorganic salts or metal complexes.

49. A compound according to claim 1 wherein:
R is selected from methylene, α-$CH_3$ and β-$CH_3$;
$R^1$ is selected from hydrogen; straight or branched $(C_1-C_8)$ alkyl group selected from methyl, ethyl, propyl, isopropyl, butyl, isobutyl, pentyl, hexyl, heptyl and octyl; straight or branched $(C_1-C_8)$alkyl group optionally substituted with α-mercapto, α-hydroxy, or amino; $(C_6-C_{10})$ aryl group selected from phenyl, α-naphthyl and β-naphthyl; $(C_7-C_9)$aralkyl group selected from benzyl, 1-phenylethyl, 2-phenylethyl and phenylpropyl; $(C_3-C_6)$ cycloalkylmethyl group selected from (cyclopropyl)methyl, (cyclobutyl)methyl, (cyclopentyl)methyl and (cyclohexyl)methyl;
$R^2$ is selected from hydrogen and $(C_1-C_6)$alkyl selected from methyl, ethyl, propyl, isopropyl, butyl, isobutyl, pentyl and hexyl;
W is selected from amino; $(C_1-C_{12})$ straight or branched alkyl monosubstituted amino group with substituents selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl, 1-methyl-1-ethylpropyl, heptyl, octyl, nonyl and decyl and the diastereomers and enantiomers of said branched alkyl monosubstituted amino group; $(C_3-C_8)$cycloalkyl monosubstituted amino group with substituents selected from cyclopropyl, trans-1,2-dimethylcyclopropyl, cis-1,2-dimethylcyclopropyl, cyclobutyl, cyclopentyl, cyclohexyl, cycloheptyl and cyclooctyl and the diastereomers and enantiomers of said $(C_3-C_8)$ cycloalkyl monosubstituted amino group; $(C_4-C_{10})$ cycloalkyl $(C_1-C_2)$alkyl monosubstituted amino group with substituents selected from (cyclopropyl)methyl, (cyclopropyl)ethyl and (cyclobutyl) methyl; $(C_3-C_{10})$ alkenyl monosubstituted amino group substituents selected from allyl, 3-butenyl, 2-butenyl (cis or trans), 2-pentenyl, 4-octenyl, 2,3-dimethyl-2-butenyl, 3-methyl-2-butenyl, 2-cyclopentenyl and 2-cyclohexenyl; $(C_7-C_{10})$aralkylamino group selected from benzylamino, 2-phenylethylamino, 1-phenylethylamino, 2-(naphthyl) methylamino, 1-(naphthyl)methylamino and phenylpropylamino; straight or branched symmetrical disubstituted $(C_2-C_8)$alkylamino group with substituents selected from dimethyl, diethyl, diisopropyl and di-n-propyl; straight or branched unsymmetrical disubstituted $(C_3-C_{14})$ alkylamino group wherein the total number of carbons in the substitution is not more than 14; unsymmetrical disubstituted $(C_4-C_{14})$ cycloalkylamino group wherein the total number of carbons in the substitution is not more than 14; $(C_1-C_4)$alkoxyamino group selected from methoxyamino, ethoxyamino, n-propoxyamino, 1-methylethoxyamino, n-butoxyamino, 2-methylpropoxyamino, and 1,1-dimethylethoxyamino; $(C_7-C_{11})$arylalkoxyamino group selected from benzyoxyamino, 2-phenylethoxyamino, 1-phenylethoxyamino, 2-(naphthyl)methoxyamino, 1-(naphthyl)-methoxy amino and phenylpropoxyamino; or $R^1$ and W taken together are —$CH_2(CH_2)_nCH_2NH$—, wherein n=1–3;
and the pharmacologically acceptable organic and inorganic salts or metal complexes.

50. A compound according to claim 1 wherein:
R is selected from α-$CH_3$;
$R^1$ is selected from hydrogen; straight or branched $(C_1-C_4)$ alkyl group selected from methyl, ethyl, propyl and butyl; straight or branched $(C_1-C_4)$alkyl group optionally substituted with amino; $(C_5-C_6)$cycloalkylmethyl group selected from (cyclopentyl)methyl and (cyclohexyl) methyl; is $R^2$ is selected from hydrogen and $(C_1-C_2)$alkyl selected from methyl and ethyl;

W is selected from amino; (C$_1$-C$_8$) straight or branched alkyl monosubstituted amino group with substituents selected from methyl, ethyl, n-propyl, 1-methylethyl, n-butyl, 1-methylpropyl, 2-methylpropyl, n-hexyl and n-octyl; (C$_3$-C$_6$)cycloalkyl monosubstituted amino group with substituents selected from cyclopropyl, cyclopentyl and cyclohexyl; (C$_4$-C$_5$)cycloalkyl (C$_1$-C$_4$) alkyl monosbustituted amino group with substituents selected from (cyclopropyl)methyl and (cyclopropyl)ethyl; (C$_3$-C$_4$) alkenyl monosubstituted amino group with substituents selected from allyl and 3-butenyl; (C$_7$-C$_{10}$)aralkylamino group selected from benzyl, 2-phenylethyl and 1-phenylethyl; straight or branched symmetrical disubstituted (C$_2$-C$_4$)alkylamino group with substituents selected form dimethyl and diethyl; straight or branched unsymmetrical disubstituted (C$_3$)alkylamino group selected from methyl(ethyl) amino; or R$^1$ and W taken together are —CH$_2$CH$_2$CH$_2$NH—; and the pharmacologically acceptable organic and inorganic salts or metal complexes.

51. A compound of the formula:

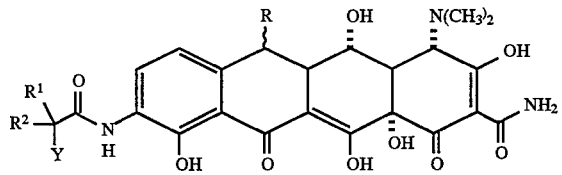

wherein:

Y is selected from (CH$_2$)$_n$X, n=0–5, X is halogen selected from bromine, chlorine, fluorine and iodine; alternatively, X is a protected amino selected from trifluoroacetylamino, (C$_7$-C$_{23}$) arylalkylamino selected from benzylamino, p-methoxybenzylamino, p-nitrobenzylamino, tritylamino and 4-methoxytritylamino;

R is selected from methylene, α-CH$_3$ and β-CH$_3$;

R$^1$ is selected from hydrogen; straight or branched (C$_1$-C$_8$) alkyl group selected from methyl, ethyl, propyl, isopropyl, butyl, isobutyl, pentyl, hexyl, heptyl and octyl; straight or branched (C$_1$-C$_8$)alkyl group optionally substituted with α-mercapto, α-hydroxy, amino, guanidino or amidino; (C$_6$-C$_{10}$)aryl group selected from phenyl, α-naphthyl and β-naphthyl; substituted (C$_6$-C$_{10}$)aryl group with substituents selected from hydroxy, halogen, (C$_1$-C$_4$)alkoxy, trihalo (C$_1$-C$_3$)alkyl, nitro, amino, and (C$_1$-C$_3$) alkylamino; (C$_7$-C$_9$)aralkyl group selected from benzyl, 1-phenylethyl, 2-phenylethyl and phenylpropyl; substituted (C$_7$-C$_9$) aralkyl group with substituents selected from halo, (C$_1$-C$_4$)alkyl, nitro, hydroxy, amino, mono- or di-substituted (C$_1$-C$_4$) alkylamino, (C$_1$-C$_4$) alkoxy, and (C$_1$-C$_4$) alkylsulfonyl; (C$_3$-C$_6$) cycloalkylmethyl group selected from (cyclopropyl)methyl, (cyclobutyl)methyl, (cyclopentyl)methyl and (cyclohexyl)methyl;

R$^2$ is selected from hydrogen and (C$_1$-C$_6$)alkyl selected from methyl, ethyl, propyl, isopropyl, butyl, isobutyl, pentyl and hexyl; and the pharmacologically acceptable organic and inorganic salts and metal complexes.

52. A compound according to claim 51, [4S-(4alpha, 12aalpha)]-9-[(bromoacetyl)amino]-4-(dimethylamino)-1,4,4a,5,5a,6,11,12a-octahydro-3,5,10,12,12a-pentahydroxy-6-methyl-1,11-dioxo-2-naphthacenecarboxamide.

53. A compound according to claim 51, [4S-(4alpha, 12aalpha)]-9-[(chloroacetyl)amino]-4-(dimethylamino)-1,4,4a,5,5a,6,11,12a-octahydro-3,5,10,12,12a-pentahydroxy-6-methyl-1,11-dioxo-2-naphthacenecarboxamide monohydrochloride.

54. A compound according to claim 51, [4S-(4alpha, 12aalpha)]-9-[(bromoacetyl)amino]-4-(dimethylamino)-1,4,4a,5,5a,6,11,12a-octahydro-3,5,10,12,12a-pentahydroxy-6-methyl-1,11-dioxo-2-naphthacenecarboxamide monohydrobromide.

55. A compound according to claim 51, [4S-(4alpha, 12aalpha)]-9-[(bromoacetyl)amino]-4-(dimethylamino)-1,4,4a,5,5a,6,11,12a-octahydro-3,5,10,12,12a-pentahydroxy-6-methyl-1,11-dioxo-2-naphthacenecarboxamide monosulfate.

56. A compound according to claim 51, [4S-(4alpha, 12aalpha)]-9-[(2-bromo-1-oxopropyl)amino]-4-(dimethylamino)-1,4,4a,5,5a,6,11,12a-octahydro-3,5,10,12,12a-pentahydroxy-6-methyl-1,11-dioxo-2-naphthacenecarboxamide monohydrobromide.

57. A compound according to claim 51, [4S-(4alpha, 12aalpha)]-9-[(2-Bromo-2-methyl-1-oxopropyl)amino]-4-(dimethylamino)-1,4,4a,5,5a,6,11,12a-octahydro-3,5,10,12,12a-pentahydroxy-6-methyl-1,11-dioxo-2-naphthacenecarboxamide hydrobromide.

58. A compound according to claim 51, [4S-(4alpha, 12aalpha)]-9-[(2-Bromo-1-oxobutyl)amino]-4-(dimethylamino)-1,4,4a,5,5a,6,11,12a-octahydro-3,5,10,12,12a-pentahydroxy-6-methyl-1,11-dioxo-2-naphthacenecarboxamide hydrobromide.

59. A compound according to claim 51, [4S-(4alpha, 12aalpha)]-9-[(2-Bromo-1-oxopentyl)amino]-4-(dimethylamino)-1,4,4a,5,5a,6,11,12a-octahydro-3,5,10,12,12a-pentahydroxy-6-methyl-1,11-dioxo-2-naphthacenecarboxamide hydrobromide.

60. A compound according to claim 51, [4S-(4alpha, 12aalpha)]-9-[(2-Bromo-2-methyl-1-oxobutyl)amino]-4-(dimethylamino)-1,4,4a,5,5a,6,11,12a-octahydro-3,5,10,12,12a-pentahydroxy-6-methyl-1,11-dioxo-2-naphthacenecarboxamide hydrobromide.

61. A compound according to claim 51, [4S-(4alpha, 12aalpha)]-9-[(2-Bromo-3-hydroxy-1-oxopropyl)amino]-4-(dimethylamino)-1,4,4a,5,5a,6,11,12a-octahydro-3,5,10,12,12a-pentahydroxy-6-methyl-1,11-dioxo-2-naphthacenecarboxamide hydrobromide.

62. A compound according to claim 51, [4S-(4alpha, 12aalpha)]-9-[(2-Bromo-3-mercapto-1-oxopropyl)amino]-4-(dimethylamino)-1,4,4a,5,5a,6,11,12,12a-pentahydroxy-6-methyl-1,11-dioxo-2-naphthacenecarboxamide hydrobromide.

63. A compound according to claim 51, [4S-(4alpha, 12aalpha)]-9-[(Bromophenylacetyl)amino]-4-(dimethylamino)-1,4,4a,5,5a,6,11,12a-octahydro-3,5,10,12,12a-pentahydroxy-6-methyl-1,11-dioxo-2-naphthacenecarboxamide hydrobromide.

64. A compound according to claim 51, [4S-(4alpha, 12aalpha)]-9-[[Bromo(4-hydroxyphenyl)acetyl]amino]-4-(dimethylamino)-1,4,4a,5,5a,6,11,12a-octahydro-3,5,10,12,12a-pentahydroxy-6-methyl-1,11-dioxo-2-naphthacenecarboxamide hydrobromide.

65. A compound according to claim 51, [4S-(4alpha, 12aalpha)]-9-[[Bromo(4-methoxyphenyl)acetyl]amino]-4-(dimethylamino)-1,4,4a,5,5a,6,11,12a-octahydro-3,5,10,12,12a-pentahydroxy-6-methyl-1,11-dioxo-2-naphthacenecarboxamide hydrobromide.

66. A compound according to claim 51, [4S-(4alpha, 12aalpha)]-9-[[Bromo[4-(trifluoromethyl)phenyl]acetyl]amino]-4-(dimethylamino)-1,4,4a,5,5a,6,11,12a-octahydro-3,5,10,12,12a-pentahydroxy-6-methyl-1,11-dioxo-2-naphthacenecarboxamide hydrobromide.

67. A compound according to claim 51, [4S-(4alpha, 12aalpha)]-9-[[Bromo[4-(dimethylamino)phenyl]acetyl]amino]-4-(dimethylamino)-1,4,4a,5,5a,6,11,12a-octahydro- 3,5,10,12,12a-pentahydroxy-6-methyl-1,11-dioxo-2-naphthacenecarboxamide hydrobromide.

68. A pharmaceutical composition of matter comprising a pharmacologically efective amount of a compound according to claim 1 in association with a pharmaceutically acceptable carrier.

69. A compound according to claim 51 wherein:

Y is selected from $(CH_2)_nX$, n=0–5, X is halogen selected from bromine, chlorine, fluorine and iodine; alternatively, X is a protected amino selected from trifluoroacetylamino, $(C_7-C_{23})$ arylalkylamino selected from benzylamino, p-methoxybenzylamino, p-nitrobenzylamino, tritylamino and 4-methoxytritylamino;

R is selected from methylene, $\alpha$-$CH_3$ and $\beta$-$CH_3$;

$R^1$ is selected from hydrogen; straight or branched $(C_1-C_8)$ alkyl group selected from methyl, ethyl, propyl, isopropyl, butyl, isobutyl, pentyl, hexyl, heptyl and octyl; straight or branched $(C_1-C_8)$alkyl group optionally substituted with $\alpha$-mercapto, and $\alpha$-hydroxy; $(C_6-C_{10})$aryl group selected from phenyl, $\alpha$-naphthyl and $\beta$-naphthyl; $(C_7-C_9)$aralkyl group selected from benzyl, 1-phenylethyl, 2-phenylethyl and phenylpropyl; substituted $(C_7-C_9)$aralkyl group with substituents selected from halo, $(C_1-C_4)$alkyl, nitro, hydroxy, amino, mono- or di-substituted $(C_1-C_4)$alkylamino, $(C_1-C_4)$alkoxy, and $(C_1-C_4)$alkylsulfonyl;

$R^2$ is selected from hydrogen and $(C_1-C_6)$alkyl selected from methyl, ethyl, propyl, isopropyl, butyl, isobutyl, pentyl and hexyl; and the pharmacologically acceptable organic and inorganic salts and metal complexes.

70. A compound according to claim 51 wherein:

Y is selected from $(CH_2)_nX$, n=0–5, X is halogen selected from bromine, chlorine, fluorine and iodine; alternatively, X is a protected amino selected from trifluoroacetylamino, $(C_7-C_{23})$ arylalkylamino selected from benzylamino and tritylamino;

R is selected from methylene, $\alpha$-$CH_3$ and $\beta$-$CH_3$;

$R^1$ is selected from hydrogen; straight or branched $(C_1-C_8)$ alkyl group selected from methyl, ethyl, propyl, isopropyl, butyl, isobutyl, pentyl, hexyl, heptyl and octyl; straight or branched $(C_1-C_8)$alkyl group optionally substituted with $\alpha$-mercapto, and $\alpha$-hydroxy; $(C_6-C_{10})$aryl group selected from phenyl, $\alpha$-naphthyl and $\beta$-naphthyl; $(C_7-C_9)$aralkyl group selected from benzyl, 1-phenylethyl, 2-phenylethyl and phenylpropyl;

$R^2$ is selected from hydrogen and $(C_1-C_6)$alkyl selected from methyl, ethyl, propyl, isopropyl, butyl, isobutyl, pentyl and hexyl; and the pharmacologically acceptable organic and inorganic salts and metal complexes.

71. A compound according to claim 51 wherein:

Y is selected from $(CH_2)_nX$, n=0–5, X is halogen selected from bromine, chlorine, fluorine and iodine; alternatively, X is a protected amino selected from triluoroacetylamino, $(C_7-C_{23})$ arylalkylamino selected from benzylamino and tritylamino;

R is selected from $\alpha$-$CH_3$;

$R^1$ is selected from hydrogen; straight or branched $(C_1-C_4)$ alkyl group selected from methyl, ethyl, propyl and butyl; straight or branched $(C_1-C_4)$alkyl group optionally substituted with amino; $(C_5-C_6)$cycloalkylmethyl group selected from (cyclopentyl)methyl and (cyclohexyl)methyl;

$R^2$ is selected from hydrogen and $(C_1-C_2)$alkyl selected from methyl and ethyl; and the pharmacologically acceptable organic and inorganic salts and metal complexes.

72. A method for the prevention, treatment or control of bacterial infections in warm-blooded animals caused by bacteria having the TetM and TetK resistant determinants which comprises administering to said animal a pharmacologically effective amount of a compound according to claim 1.

\* \* \* \* \*